United States Patent
Hyldig-Nielsen et al.

(10) Patent No.: US 6,664,045 B1
(45) Date of Patent: Dec. 16, 2003

(54) PNA PROBES, PROBE SETS, METHODS AND KITS PERTAINING TO THE DETECTION OF MICROORGANISMS

(75) Inventors: Jens J. Hyldig-Nielsen, Holliston, MA (US); James M. Coull, Westford, MA (US)

(73) Assignee: Boston Probes, Inc., Bedford, MA (US)

( * ) Notice: Subject to any disclaimer, the term of this patent is extended or adjusted under 35 U.S.C. 154(b) by 0 days.

(21) Appl. No.: 09/335,629

(22) Filed: Jun. 18, 1999

Related U.S. Application Data

(60) Provisional application No. 60/089,737, filed on Jun. 18, 1998, now abandoned.

(51) Int. Cl.[7] ............... C12Q 1/68; C07H 21/00; C07H 21/02
(52) U.S. Cl. ............... 435/6; 435/7.1; 435/91.1; 435/91.2; 536/22.1; 536/23.1; 536/25.3
(58) Field of Search ............ 435/5, 6, 7.1, 91.1, 435/91.2; 536/22.1, 23.1, 25.3

(56) References Cited

U.S. PATENT DOCUMENTS

| | | | |
|---|---|---|---|
| 4,816,389 A | 3/1989 | Sansonetti et al. | ............ 435/6 |
| 4,992,364 A | 2/1991 | Sansonetti et al. | ............ 435/6 |

(List continued on next page.)

FOREIGN PATENT DOCUMENTS

| EP | 0531798 B1 | 1/1984 | |
|---|---|---|---|
| EP | 0133288 A2 | 7/1984 | |
| EP | 0395292 A2 | 4/1990 | |
| EP | 0497464 A1 | 1/1992 | |
| EP | 0632269 A1 | 6/1994 | |
| WO | WO89/11548 | 11/1989 | |
| WO | WO90/01560 | 2/1990 | |
| WO | WO90/01564 | 2/1990 | |
| WO | WO92/15708 | 9/1992 | |
| WO | WO 92/20702 | * 11/1992 | ............ C07K/7/00 |
| WO | WO94/19490 | 9/1994 | |
| WO | WO95/32305 | 11/1995 | |
| WO | WO96/17956 | 6/1996 | |
| WO | WO97/14026 | 4/1997 | |
| WO | WO97/18325 | 5/1997 | |
| WO | WO98/03678 | 1/1998 | |
| WO | WO98/15648 | 4/1998 | |

OTHER PUBLICATIONS

Good et al. "Inhibition of translation and bacterial growth by peptide nucleic acid targeted to ribosomal RNA" PNAS vol. 95, pp. 2073–2076, Mar. 1998.*

(List continued on next page.)

*Primary Examiner*—Jezia Riley
(74) *Attorney, Agent, or Firm*—Brian D. Gildea

(57) ABSTRACT

This invention is related to novel PNA probes, probe sets, methods and kits pertaining to the detection of microorganisms. The probes, probe sets, methods and kits of this invention can be used to detect, identify or quantitate one or more organisms in a sample wherein the organisms are selected from the group consisting of *E. coli, Staphylococcus aureus, Pseudomonas aeruginosa, Pseudomonas cepatia, Pseudomonas fluorescens* or organisms of a bacterial genus including the Salmonella genus, Bacillus genus or Pseudomonas genus. The preferred probing nucleobase sequence of the PNA probes used to detect the bacteria listed above are TCA-ATG-AGC-AAA-GGT (*E. coli*); GCT-TCT-CGT-CCG-TTC (*Staphylococcus aureus*); CTG-AAT-CCA-GGA-GCA and AAC-TTG-CTG-AAC-CAC (*Pseudomonas aeruginosa*); CCA-TCG-CAT-CTA-ACA (*Pseudomonas cepatia*); TCT-AGT-CAG-TCA-GTT (*Pseudomonas fluorescens*); CCG-ACT-TGA-CAG-ACC and CCT-GCC-AGT-TTC-GAA (Salmonella genus); CTT-TGT-TCT-GTC-CAT (Bacillus genus); GCT-GGC-CTA-GCC-TTC, GTC-CTC-CTT-GCG-GTT and TTC-TCA-TCC-GCT-CGA (Pseudomonas genus). The PNA probes, probe sets, methods and kits of this invention are particularly well suited for use in multiplex PNA-FISH assays.

47 Claims, 3 Drawing Sheets

(1 of 3 Drawing Sheet(s) Filed in Color)

U.S. PATENT DOCUMENTS

| | | | |
|---|---|---|---|
| 5,041,372 A | 8/1991 | Lampel et al. | 435/6 |
| 5,089,386 A * | 2/1992 | Stackebrandt et al. | 435/6 |
| 5,147,778 A | 9/1992 | Nietupski et al. | 435/6 |
| 5,486,454 A | 1/1996 | Madonna et al. | 435/6 |
| 5,495,008 A | 2/1996 | Lane et al. | 536/24.3 |
| 5,574,145 A | 11/1996 | Barry et al. | 536/24.32 |
| 5,582,974 A | 12/1996 | Nietupski et al. | 435/6 |
| 5,612,458 A | 3/1997 | Hyldig-Nielsen et al. | 530/388.21 |
| 5,648,481 A | 7/1997 | Parodos et al. | 536/24.32 |
| 5,654,417 A | 8/1997 | Tarr et al. | 536/24.32 |
| 5,677,127 A | 10/1997 | Hogan et al. | 435/6 |
| 5,693,469 A | 12/1997 | Hogan | 435/6 |
| 5,714,321 A | 2/1998 | Hogan | 435/6 |
| 5,723,344 A | 3/1998 | Mabilat et al. | 436/518 |
| 5,888,733 A | 3/1999 | Hyldig-Nielsen et al. | 435/6 |
| 5,888,734 A | 3/1999 | Cremer et al. | 435/6 |
| 5,985,563 A | 11/1999 | Hyldig-Nielsen et al. | 435/6 |
| 6,004,754 A * | 12/1999 | You | 435/6 |
| 6,214,545 B1 * | 4/2001 | Dong et al. | 435/6 |

OTHER PUBLICATIONS

Good et al. "Antisense inhibition of gene expression in bacteria by PNA targeted to mRNA" Nature Biotechnology, vol. 16, pp. 355–358, Apr. 1998.*

Amann, R.I. et al, Fluorescent–oligonucleotide probing of whole cells for determinative, phylogenetic, and environmental studies in microbiology. J. Bacteriology 172, 762–770 (1990).

Amann, R.I. et al, Combination of 16S rRNA–targeted oligonucleotide probes with flow cytometry for analyzing mixed microbial populations. Appl. and Environ. Microbiol. 56, 1919–1925 (1990).

Amann, R. et al, Identification in situ and phylogeny of uncultured bacterial endosymbionts. Nature 351, 161–164 (1991).

Amann, R. I. et al, Phylogenetic identification and in situ detection of individual microbial cells without cultivation. Microbio. Reviews 59, 143–169 (1995).

Bauman, J.G.J. et al, Flow cytometric detection for ribosomal RNA in suspended cells by fluorescent in situ hybridization. Cytometry 9, 517–524 (1988).

DeLong, E.F. et al., Phylogenetic stains: ribosomal RNA–based probes for the identification of single cells. Science 243, 1360–1363 (1989).

DeLong, E.F. et al, Fluorescent, ribosomal RNA probes for clinical application: a research review. Diagnos. & Clin. Testing 28, 41–44 (1990).

Fuchs, B.M. et al, Flow cytometric analysis of the in situ accessibility of escherichia coli 16S rRNA for fluorescently labeles oligonucleotide probes. Appl. and Environ. Microbiol. 64, 4973–4982 (1998).

Fuchs, B.M. et al, Flow cytometric analysis of the in situ accessibility of *escherichia coli* 16S rRNA for fluorescently labeled oligonucleotide probes. Appl. and Environ. Microbiol. 64, 4973–4982 (1998).

Hahn, D. et al., Oligonucleotide probes that hybridize with rRNA as a tool to study Frankia stains in root nodules. Applied and Environ. Microbiol. 56, 1342–1346 (1990).

Hahn, D. et al, Extraction of ribosomal RNA from soil for detection of Frankia with oligonucleotide probes. Arch. Microbiol. 154, 329–335 (1990).

Hahn, D. et al, Detection of micro–organisms in soil after in situ hybridization with rRNA–targeted, fluorescently labelled oligonucelotides. J. Gen. Microbiol. 138, 879–887 (1992).

Heidelberg, J.F. et al, Enumeration of *Vibrio vulnificus* on membrane filters with a fluorescently labeled oligonucleotide probe specific for kingdom–level 16S rRNA sequences. Appl. and Environ. Microbiol. 59, 3474–3476 (1993).

Heiles, H.B.J. et al, In situ hybridization with digoxigenin–labeled DNA of human papillomaviruses (HPV 16/18) in HeLa and SiHa cells. BioTechniques 6, 978–981 (1988).

Herron, P.R. et al, New method for extraction of streptomycete spores from soil and application to the study of lysogeny in sterile amended and nonsteril soil. Appl. and Environ. Microbiol. 56, 1406–1412 (1990).

Holben, W.E. et al, DNA probe method for the detection of specific microorganisms in the soil bacterial community. Appl. and Environ. Microbiol. 54, 703–711 (1988).

Just, T. et al, Flow cytometric detection of EBV (EBER snRNA) using peptide nucleic acid probes. J. Virol. Methods 73, 163–174 (1998).

Lansdorp, P.M., Close encounters of the PNA kind. Nature Biotech. 14, 1653 (1996).

Lansdorp, P.M. et al, Telomeres in the haemopoietic system. Telomers and Telomerase (eds. DJ Chadwick & G. Cardew), John Wiley & Sons Ltd., West Suxxes, UK, pp 209–222 (1997).

Lansdorp, P.M. et al, Heterogeneity in tleomere length of human chromosomes. Human Mol. Gen. 5m 685–691 (1996).

Seal, S.E. et al, Differentiation of Pseudomonas solanacearum, Pseudomonas syzygii, Pseudomonas picketti and the blood disease bacterium by partial 16S rRNA sequencing: construction of oligonucleotide primers for sensitive detection by polymerase chain reaction. J. Gen. Microbiol. 139, 1587–1594 (1993).

Taneja, K.L., Localization of trinucleotide repeat sequences in myotonic dystrophy cells using a single fluorochrome–labeled PNA probe. BioTechniques 24, 472–76 (1998).

Thisted, M. et al, Detection of immunoglobulin kappa light chain mRNA in paraffin sections by in situ hybridization using peptide nucleic acid probes. Cell Vision 3, 358–363 (1996).

Ward, D.M. et al, 16S rRNA sequences reveal numerous uncultured microorganisms in a natural community. Nature 345, 63–65 (1990).

Weisburg, W.G. et al, 16S Ribosomal DNA amplification for phylogenetic study. J. Bacteriol. 173, 697–703 (1991).

Zarda, B. et al, Identification of single bacterial cells using digoxigenin–labelled, rRNA–targeted oligonucleotides. J. Gen. Microbiol. 137, 2823–2830 (1991).

Stefano, K. et al, Diagnostic Applications of PNA Oligomers. Diagnostic Gene Detection and Quantification Technologies for Infectious Agents and Human Genetic Diseases. #948 IBC Library Series, 19–37 (1997).

Pluskal, M. et al, Peptide Nucleic Acid Probes and their Application in DNA and RNA Blot Hybridization Analysis. American Society for Biochemistry and Molecular Biology. Abstract #35. 85th Annual Meeting, Wahington, DC May 21–25, 1994.

* cited by examiner

Species Specific Probes

Fig 1-I
Probe #FLU-1

A B C D E F G H I

Fig. 1-II
Probe #Flu-2

A B C D E F G H I

Fig. 1-III
Probe # Flu-3 & Flu-4

B A C D E F G H I

Fig. 1-IV
Probe # Flu-5

A B C D E F G H I

Fig. 1-V
Probe # Flu-6

A B C D E F G H I

Genus Specific Probes

Fig. 2-I
Probe# Flu-7 & Flu-8 & Flu-9
A B C D E F G H I

Fig. 2-II
Probe # Flu-10
A B C D E F G H I

Fig. 2-III
Probe # Flu-11
A B C D E F G H I

Fig. 2-IV
Probe # Flu-12
A B C D E F G H I

Figure 3 (color)
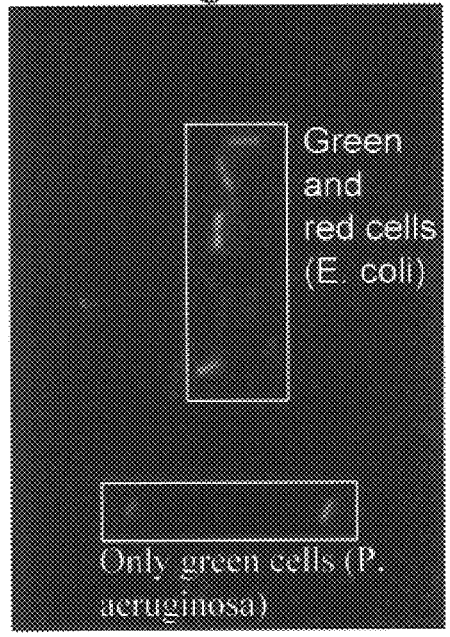
Green image
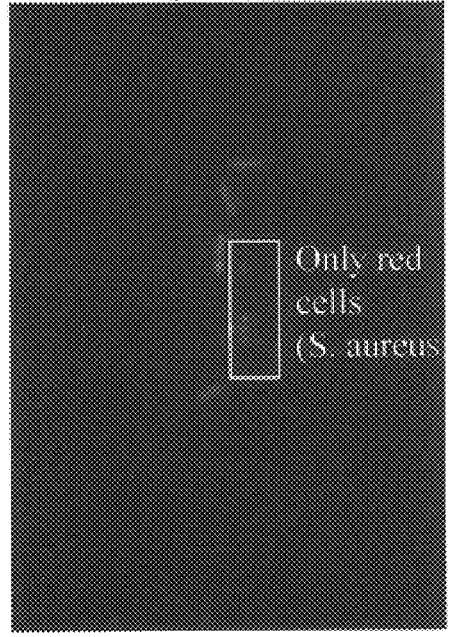
Red image
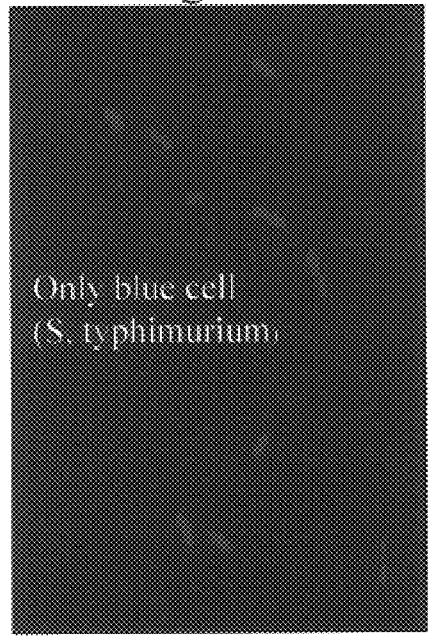
Blue image
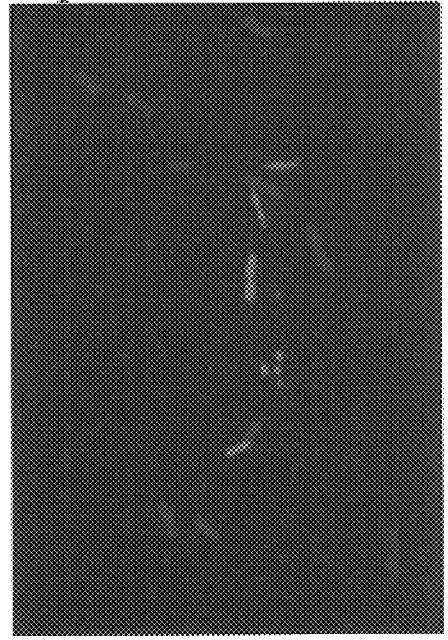
Composite red and blue image

SEQUENCE LISTING

```
<160> NUMBER OF SEQ ID NOS: 12

<210> SEQ ID NO 1
<211> LENGTH: 15
<212> TYPE: DNA
<213> ORGANISM: Artificial Sequence
<220> FEATURE:
<223> OTHER INFORMATION: Description of Combined DNA/RNA Molecule:PNA
      Probing Nucleobase Sequence
<220> FEATURE:
<223> OTHER INFORMATION: Description of Artificial Sequence:PNA Probing
      Nucleobase Sequence

<400> SEQUENCE: 1
tcaatgagca aaggt                                                            15

<210> SEQ ID NO 2
<211> LENGTH: 15
<212> TYPE: DNA
<213> ORGANISM: Artificial Sequence
<220> FEATURE:
<223> OTHER INFORMATION: Description of Combined DNA/RNA Molecule:PNA
      Probing Nucleobase Sequence
<220> FEATURE:
<223> OTHER INFORMATION: Description of Artificial Sequence:PNA Probing
      Nucleobase Sequence

<400> SEQUENCE: 2
gcttctcgtc cgttc                                                            15

<210> SEQ ID NO 3
<211> LENGTH: 15
<212> TYPE: DNA
<213> ORGANISM: Artificial Sequence
<220> FEATURE:
<223> OTHER INFORMATION: Description of Combined DNA/RNA Molecule:PNA
      Probing Nucleobase Sequence
<220> FEATURE:
<223> OTHER INFORMATION: Description of Artificial Sequence:PNA Probing
      Nucleobase Sequence

<400> SEQUENCE: 3
ctgaatccag gagca                                                            15

<210> SEQ ID NO 4
<211> LENGTH: 15
<212> TYPE: DNA
<213> ORGANISM: Artificial Sequence
<220> FEATURE:
<223> OTHER INFORMATION: Description of Combined DNA/RNA Molecule:PNA
      Probing Nucleobase Sequence
<220> FEATURE:
<223> OTHER INFORMATION: Description of Artificial Sequence:PNA Probing
```

-continued

Nucleobase Sequence

<400> SEQUENCE: 4
aacttgctga accac                                                          15

<210> SEQ ID NO 5
<211> LENGTH: 15
<212> TYPE: DNA
<213> ORGANISM: Artificial Sequence
<220> FEATURE:
<223> OTHER INFORMATION: Description of Combined DNA/RNA Molecule:
      Probing Nucleobase Sequence
<220> FEATURE:
<223> OTHER INFORMATION: Description of Artificial Sequence:PNA Probing
      Nucleobase Sequence

<400> SEQUENCE: 5
ccatcgcatc taaca                                                          15

<210> SEQ ID NO 6
<211> LENGTH: 15
<212> TYPE: DNA
<213> ORGANISM: Artificial Sequence
<220> FEATURE:
<223> OTHER INFORMATION: Description of Combined DNA/RNA Molecule:PNA
      Probing Nucleobase Sequence
<220> FEATURE:
<223> OTHER INFORMATION: Description of Artificial Sequence:PNA Probing
      Nucleobase Sequence

<400> SEQUENCE: 6
tctagtcagt cagtt                                                          15

<210> SEQ ID NO 7
<211> LENGTH: 15
<212> TYPE: DNA
<213> ORGANISM: Artificial Sequence
<220> FEATURE:
<223> OTHER INFORMATION: Description of Combined DNA/RNA Molecule:PNA
      Probing Nucleobase Sequence
<220> FEATURE:
<223> OTHER INFORMATION: Description of Artificial Sequence:PNA Probing
      Nucleobase Sequence

<400> SEQUENCE: 7
gctggcctag ccttc                                                          15

<210> SEQ ID NO 8
<211> LENGTH: 15
<212> TYPE: DNA
<213> ORGANISM: Artificial Sequence
<220> FEATURE:
<223> OTHER INFORMATION: Description of Combined DNA/RNA Molecule:PNA
      Probing Nucleobase Sequence
<220> FEATURE:
<223> OTHER INFORMATION: Description of Artificial Sequence:PNA Probing
      Nucleobase Sequence

<400> SEQUENCE: 8
gtcctccttg cggtt                                                          15

<210> SEQ ID NO 9
<211> LENGTH: 15
<212> TYPE: DNA
<213> ORGANISM: Artificial Sequence
<220> FEATURE:
<223> OTHER INFORMATION: Description of Combined DNA/RNA Molecule:PNA
      Probing Nucleobase Sequence
<220> FEATURE:

-continued

```
<223> OTHER INFORMATION: Description of Artificial Sequence:PNA Probing
      Nucleobase Sequence

<400> SEQUENCE: 9
ttctcatccg ctcga                                                          15

<210> SEQ ID NO 10
<211> LENGTH: 15
<212> TYPE: DNA
<213> ORGANISM: Artificial Sequence
<220> FEATURE:
<223> OTHER INFORMATION: Description of Combined DNA/RNA Molecule:PNA
      Probing Nucleobase Sequence
<220> FEATURE:
<223> OTHER INFORMATION: Description of Artificial Sequence:PNA Probing
      Nucleobase Sequence

<400> SEQUENCE: 10
ccgacttgac agacc                                                          15

<210> SEQ ID NO 11
<211> LENGTH: 15
<212> TYPE: DNA
<213> ORGANISM: Artificial Sequence
<220> FEATURE:
<223> OTHER INFORMATION: Description of Combined DNA/RNA Molecule:PNA
      Probing Nucleobase Sequence
<220> FEATURE:
<223> OTHER INFORMATION: Description of Artificial Sequence:PNA Probing
      Nucleobase Sequence

<400> SEQUENCE: 11
cctgccagtt tcgaa                                                          15

<210> SEQ ID NO 12
<211> LENGTH: 15
<212> TYPE: DNA
<213> ORGANISM: Artificial Sequence
<220> FEATURE:
<223> OTHER INFORMATION: Description of Combined DNA/RNA Molecule:PNA
      Probing Nucleobase Sequence
<220> FEATURE:
<223> OTHER INFORMATION: Description of Artificial Sequence:PNA Probing
      Nucleobase Sequence

<400> SEQUENCE: 12
ctttgttctg tccat                                                          15
```

PNA PROBES, PROBE SETS, METHODS AND KITS PERTAINING TO THE DETECTION OF MICROORGANISMS

CROSS REFERENCE TO RELATED APPLICATIONS

This application claims the benefit of U.S. Provisional Patent Application Serial No. 60/089,737 filed on Jun. 18, 1998 now abandoned.

BACKGROUND OF THE INVENTION

1. Field of the Invention

This invention is related to the field of probe-based detection, analysis and quantitation of microorganisms. More specifically, this invention relates to novel PNA probes, probe sets, methods and kits pertaining for the detection of microorganisms. The PNA probes, probe sets, methods and kits of this invention can be used to detect, identify or quantitate one or more organisms in a sample wherein the organisms of interest may include *E. coli, Staphylococcus aureus, Pseudomonas aeruginosa, Pseudomonas cepatia, Pseudomonas fluorescens* or organisms of a bacterial genus including the Salmonella genus, Bacillus genus or Pseudomonas genus.

2. Description of the Related Art

Nucleic acid hybridization is a fundamental process in molecular biology. Probe-based assays are useful in the detection, quantitation and analysis of nucleic acids. Nucleic acid probes have long been used to analyze samples for the presence of nucleic acid from bacteria, fungi, virus or other organisms and are also useful in examining genetically-based disease states or clinical conditions of interest. Nonetheless, probe-based assays have been slow to achieve commercial success. This lack of commercial success is, at least partially, the result of difficulties associated with specificity, sensitivity and reliability.

Hybridization assays hold promise as a means to screen large numbers of samples for conditions of interest. In practice, however, it is often difficult to multiplex a hybridization assay given the requirement that each of the many very different probes in the assay must exhibit a very high degree of specificity for a specific target nucleic acid under the same or similar conditions of stringency. Given the difficulties in specificity, sensitivity and reliability of nucleic acid probes in assays designed to detect a single target nucleic acid, sensitive and reliable methods for the multiplex analysis of samples has been particularly elusive.

Despite its name, Peptide Nucleic Acid (PNA) is neither a peptide, a nucleic acid nor is it an acid. Peptide Nucleic Acid (PNA) is a non-naturally occurring polyamide which can hybridize to nucleic acid (DNA and RNA) with sequence specificity (See: U.S. Pat. No. 5,539,082 and Egholm et al., *Nature* 365: 566–568 (1993)). Being a non-naturally occurring molecule, unmodified PNA is not known to be a substrate for the enzymes which are known to degrade peptides or nucleic acids. Therefore, PNA should be stable in biological samples, as well as have a long shelf-life. Unlike nucleic acid hybridization which is very dependent on ionic strength, the hybridization of a PNA with a nucleic acid is fairly independent of ionic strength and is favored at low ionic strength, conditions which strongly disfavor the hybridization of nucleic acid to nucleic acid (Egholm et al., *Nature*, at p. 567). The effect of ionic strength on the stability and conformation of PNA complexes has been extensively investigated (Tomac et al., *J. Am. Chem. Soc.* 118:55 44–5552 (1996)). Sequence discrimination is more efficient for PNA recognizing DNA than for DNA recognizing DNA (Egholm et al., *Nature*, at p. 566). However, the advantages in point mutation discrimination with PNA probes, as compared with DNA probes, in a hybridization assay, appears to be somewhat sequence dependent (Nielsen et al., *Anti-Cancer Drug Design* 8:53–65, (1993) and Weiler et al., *Nucl. Acids Res.* 25: 2792–2799 (1997)).

Though they hybridize to nucleic acid with sequence specificity (See: Egholm et al., *Nature*, at p. 567), PNAs have been slow to achieve commercial success at least partially due to cost, sequence specific properties/problems associated with solubility and self-aggregation (See: Bergman, F., Bannwarth, W. and Tam, S., *Tett. Lett.* 36:6823–6826 (1995), Haaima, G., Lohse, A., Buchardt, O. and Nielsen, P. E., *Angew. Chem. Int. Ed. Engl.* 35:1939–1942 (1996) and Lesnik, E., Hassman, F., Barbeau, J., Teng, K. and Weiler, K., *Nucleosides & Nucleotides* 16:1775–1779 (1997) at p 433, col. 1, ln. 28 through col. 2, ln. 3) as well as the uncertainty pertaining to non-specific interactions which might occur in complex systems such as a cell (See: Good, L. et al., *Antisense & Nucleic Acid Drug Development* 7:431–437 (1997)). However, problems associated with solubility and self-aggregation have recently been reduced or eliminated (See: Gildea et al., *Tett. Lett.* 39: 7255–7258 (1998)). Nevertheless, their unique properties clearly demonstrate that PNA is not the equivalent of a nucleic acid in either structure or function. Consequently, PNA probes need to be evaluated for performance and optimization to thereby confirm whether they can be used to specifically and reliably detect a particular nucleic acid target sequence, particularly when the target sequence exists in a complex sample such as a cell, tissue or organism.

In summary, any method, kits or compositions which could improve the specificity, sensitivity and reliability of probe-based assays for the detection of microorganisms in samples of interest would be a useful advance in the state of the art particularly where the methods were uniformly applicable to probes of all or substantially all sequence variations. Moreover, the methods, kits or compositions would be particularly useful if they could provide for the rapid, reliable and sensitive multiplex analysis of samples for the presence of microorganisms such as bacteria.

SUMMARY OF THE INVENTION

This invention is directed to PNA probes, probe sets, methods and kits useful for detecting, identifying and/or quantitating one or more organisms of interest in a sample wherein the organisms are members of the bacterial species of *E. coli, Staphylococcus aureus, Pseudomonas aeruginosa, Pseudomonas cepatia, Pseudomonas fluorescens* or organisms of a bacterial genus including the Salmonella genus, Bacillus genus or Pseudomonas genus. The PNA probes and probe sets of this invention comprise probing nucleobase sequences which allow for the specific detection of bacteria of a target species or genus.

The preferred probing nucleobase sequence of the probes of this invention are listed in Table 1, below. In preferred embodiments, PNA probes are organized into a set which is designed to detect, identify or quantitate certain species of bacteria, certain genus of bacteria or members of a defined set of species and genus of bacteria. In a most preferred embodiment, the probe set is suitable for the detection, identification and/or quantitation of USP bacteria (as defined herein).

This invention is further directed to a method suitable for detecting, identifying and/or quantitating one or more organisms of interest in a sample wherein the organisms are members of the bacterial species of *E. coli, Staphylococcus aureus, Pseudomonas aeruginosa, Pseudomonas cepatia, Pseudomonas fluorescens* or organisms of a bacterial genus including the Salmonella genus, Bacillus genus or Pseudomonas genus. The method comprises contacting the sample with one or more PNA probes, wherein suitable probes are described herein. According to the method, the presence, absence or number of the one or more organisms of interest in the sample are then detected, identified or quantitated. Detection, identification and or quantitation is made possible by correlating the hybridization, under suitable hybridization conditions or suitable in-situ hybridization conditions, of the probing nucleobase sequence of a PNA probe to the target sequence with the presence, absence or number of the target organism of interest in the sample. This correlation is made possible by direct or indirect detection of the probe/target sequence hybrid.

In yet another embodiment, this invention is directed to kits suitable for performing an assay which detects the presence, absence or number of one or more organisms of interest in a sample. The kits of this invention comprise one or more PNA probes and other reagents or compositions which are selected to perform an assay or otherwise simplify the performance of an assay.

The PNA probes, probe sets, methods and kits of this invention have been demonstrated to be highly specific for the target organism(s) for which they are intended to detect. Moreover, the assays described herein are rapid (2–3 hours or less), sensitive, reliable and capable of both identification as well as enumeration of organisms listed in Table 1 in a single assay. Since probe-based analysis generically detects nucleic acid, the analysis of cells in culture is preferably used to distinguish between viable organisms and dead (non-viable) organisms, the presence of which are generally not considered to cause spoilage or contamination.

This invention is also directed to a multiplex PNA-fluorescent in-situ hybridization (FISH) assay. As a demonstration of the versatility of the PNA probes, probe sets, methods and kits of this invention, a PNA-FISH assay was multiplexed without any change to the protocol. The analysis was rapid, sensitive and reliable despite the substantial sequence variations of the probing nucleobase sequence of the PNA probes used for the different target organisms. Thus, Applicants have demonstrated (believed to be the first successful example) the feasibility of a multiplex PNA-FISH assay which can positively detect, identify and quantitate two or more target organisms in a single assay. Specifically, the multiplex assay as described in Example 10 provided a means for the detection, identification and quantitation of four target organisms using only three independently detectable moieties (fluorophores).

The PNA probes, probe sets, methods and kits of this invention are particularly useful for the detection of bacteria (pathogens) in food, beverages, water, pharmaceutical products, personal care products, dairy products or environmental samples. The analysis of preferred beverages include soda, bottled water, fruit juice, beer, wine or liquor products. Suitable PNA probes, probe sets, methods and kits will be particularly useful for the analysis of raw materials, equipment, products or processes used to manufacture or store food, beverages, water, pharmaceutical products, personal care products dairy products or environmental samples.

Additionally, the PNA probes, probe sets, methods and kits of this invention are particularly useful for the detection of bacteria (pathogens) in clinical samples and clinical environments. Suitable PNA probes, probe sets, methods and kits will be particularly useful for the analysis of clinical specimens, equipment, fixtures or products used to treat humans or animals.

BRIEF DESCRIPTION OF THE DRAWINGS

This patent or application file contains at least one drawing executed in color. Copies of this patent or patent application publication with color drawing(s) will be provided by the Office upon request and payment of necessary fee.

FIGS. 3I through 3IV are individual or composite digital images of the same section of a sample slide of bacteria hybridized with PNA probes wherein the PNA probes are independently detectable. The images were obtained using a fluorescent microscope and three different commercially available light filters. FIG. 3I is the image obtained using a Green filter; Image 3-II is the image obtained using a Red filter, FIG. 3-III is the image obtained using a Blue filter and FIG. 3-IV is a digital composite of Images 3-II and 3-III.

DETAILED DESCRIPTION OF THE INVENTION

Figure 1:
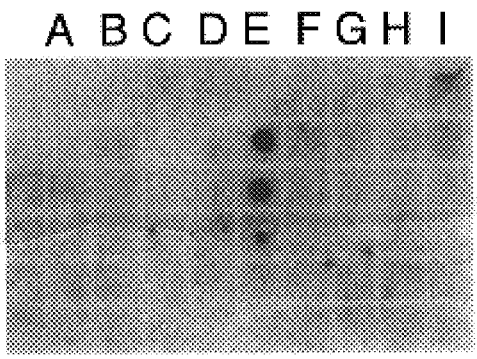
FIGS. 1-I through 1-V are electronic images of dot blot assays used to examine the specificity of PNA oligomers for certain target organisms of a bacterial species.
Figure 1:
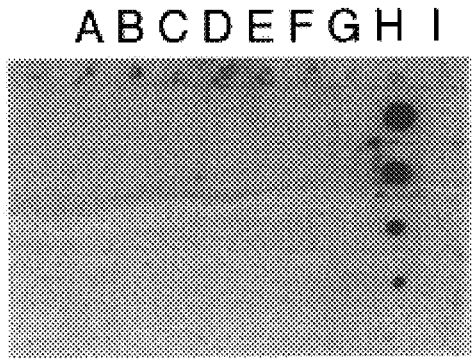
Figure 1:
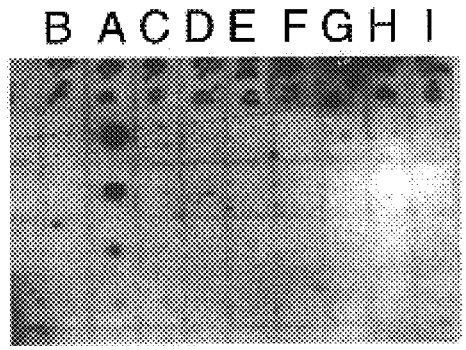
Figure 1:
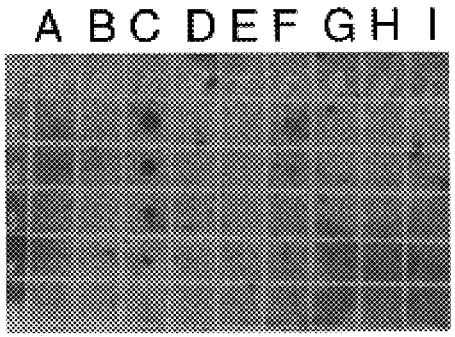
Figure 1:
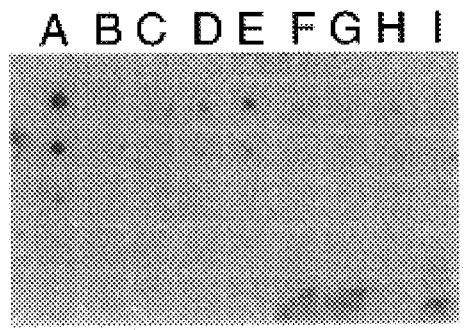

1. Definitions a. As used herein, the term "nucleobase" shall include those naturally occurring and those non-naturally occurring heterocyclic moieties commonly known to those who utilize nucleic acid technology or utilize peptide nucleic acid technology to thereby generate polymers which can sequence specifically bind to nucleic acids.

b. As used herein, the term "nucleobase sequence" is any segment of a polymer which comprises nucleobase containing subunits. Non-limiting examples of suitable polymers or polymers segments include oligonucleotides, oligoribonucleotides, peptide nucleic acids, nucleic acid analogs, nucleic acid mimics or chimeras.

c. As used herein, the term "target sequence" is the nucleic acid nucleobase sequence of a specific bacteria which is to be detected in an assay and to which at least a portion of the probing nucleobase sequence of the bacteria specific probe is designed to hybridize.

d. As used herein, the term "peptide nucleic acid" or "PNA" shall be defined as any oligomer, linked polymer or chimeric oligomer, comprising two or more PNA subunits (residues), including any of the compounds referred to or claimed as peptide nucleic acids in U.S. Pat. Nos. 5,539,082, 5,527,675, 5,623,049, 5,714,331, 5,736,336, 5,773,571 or 5,786,461 (all of which are herein incorporated by reference). The term "peptide nucleic acid" or "PNA" shall also apply to polymers comprising two or more subunits of those nucleic acid mimics described in the following publications: Diderichsen et al., *Tett. Lett.* 37: 475–478 (1996); Fujii et al., *Bioorg. Med. Chem. Lett.* 7: 637–627 (1997); Jordan et al., *Bioorg. Med. Chem. Lett.* 7: 687–690 (1997); Krotz et al., *Tett. Lett.* 36: 6941–6944 (1995); Lagriffoul et al., *Bioorg. Med. Chem. Lett.* 4: 1081–1082 (1994); Lowe et al., *J. Chem. Soc. Perkin Trans.* 1, (1997) 1: 539–546; Lowe et al., *J. Chem. Soc. Perkin Trans.* 11: 547–554 (1997); Lowe et al., *J. Chem. Soc. Perkin Trans.* 1 1:5 55–560 (1997); Petersen et al., *Bioorg. Med. Chem. Lett.* 6: 793–796 (1996); Diederichsen, U., *Bioorganic & Med. Chem. Lett.*, 8: 165–168 (1998); Cantin et al., *Tett. Lett.*, 38: 4211–4214 (1997); Ciapetti et al., *Tetrahedron*, 53: 1167–1176 (1997) and Lagriffoule et al., *Chem. Eur. J.*, 3: 912–919 (1997).

In preferred embodiments, a PNA is a polymer comprising two or more subunits of the formula:

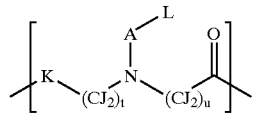

wherein, each J is the same or different and is selected from the group consisting of H, $R^1$, $OR^1$, $SR^1$, $NHR^1$, $NR^1_2$, F, Cl, Br and I. Each K is the same or different and is selected from the group consisting of O, S, NH and $NR^1$. Each $R^1$ is the same or different and is an alkyl group having one to five carbon atoms which may optionally contain a heteroatom or a substituted or unsubstituted aryl group. Each A is selected from the group consisting of a single bond, a group of the formula; —$(CJ_2)_s$— and a group of the formula; —$(CJ_2)_sC(O)$—, wherein, J is defined above and each s is an integer from one to five. The integer t is 1 or 2 and the integer u is 1 or 2. Each L is the same or different and is independently selected from the group consisting of J, adenine, cytosine, guanine, thymine, uridine, 5-methylcytosine, 2-aminopurine, 2-amino-6-chloropurine, 2,6-diaminopurine, hypoxanthine, pseudoisocytosine, 2-thiouracil, 2-thiothymidine, other naturally occurring nucleobase analogs, other non-naturally occurring nucleobases, substituted and unsubstituted aromatic moieties, biotin, fluorescein and dabcyl. In the most preferred embodiment, a PNA subunit consists of a naturally occurring or non-naturally occurring nucleobase attached to the aza nitrogen of the N-[2-(aminoethyl)]glycine backbone through a methylene carbonyl linkage.

e. As used herein, the terms "label" and "detectable moiety" shall be interchangeable and shall refer to moieties which can be attached to a PNA probe, antibody or antibody fragment to thereby render the probe, antibody or antibody fragment detectable by an instrument or method.

f. As used herein, the term "chimera" or "chimeric oligomer" shall mean an oligomer comprising two or more linked subunits which are selected from different classes of subunits. For example, a PNA/DNA chimera would comprise at least two PNA subunits linked to at least one 2'-deoxyribonucleic acid subunit (For exemplary methods and compositions related to PNA/DNA chimera preparation See: WO96/40709). Exemplary component subunits of the chimera are selected from the group consisting of PNA subunits, naturally occurring amino acid subunits, DNA subunits, RNA subunits and subunits of analogues or mimics of nucleic acids.

g. As used herein, the term "linked polymer" shall mean a polymer comprising two or more polymer segments which are linked by a linker. The polymer segments which are linked to form the linked polymer are selected from the group consisting of an oligodeoxynucleotide, an oligoribonucleotide, a peptide, a polyamide, a peptide nucleic acid (PNA) and a chimera.

2. Description

I. General

PNA Synthesis:

Methods for the chemical assembly of PNAs are well known (See: U.S. Pat. Nos. 5,539,082, 5,527,675, 5,623,049, 5,714,331, 5,736,336, 5,773,571 or 5,786,571, herein incorporated by reference). Chemicals and instrumentation for the support bound automated chemical assembly of peptide nucleic acids are now commercially available. Both labeled and unlabeled PNA oligomers are likewise available from commercial vendors of custom PNA oligomers. Chemical assembly of a PNA is analogous to solid phase peptide synthesis, wherein at each cycle of assembly the oligomer possesses a reactive alkyl amino terminus which is condensed with the next synthon to be added to the growing polymer. Because standard peptide chemistry is utilized, natural and non-natural amino acids are routinely incorporated into a PNA oligomer. Because a PNA is a polyamide, it has a C-terminus (carboxyl terminus) and an N-terminus (amino terminus). For the purposes of the design of a hybridization probe suitable for antiparallel binding to the target sequence (the preferred orientation), the N-terminus of the probing nucleobase sequence of the PNA probe is the equivalent of the 5'-hydroxyl terminus of an equivalent DNA or RNA oligonucleotide.

PNA Labeling:

Preferred non-limiting methods for labeling PNAs are described in WO98/24933, WO99/22018 WO99/21881, the examples section of this specification or are otherwise well known in the art of PNA synthesis.

Labels:

Non-limiting examples of detectable moieties (labels) suitable for labeling PNA probes or antibodies used in the practice of this invention would include a dextran conjugate, a branched nucleic acid detection system, a chromophore, a fluorophore, a spin label, a radioisotope, an enzyme, a hapten, an acridinium ester and a chemiluminescent compound. Other suitable labeling reagents and preferred methods of attachment would be recognized by those of ordinary skill in the art of PNA, peptide or nucleic acid synthesis.

Preferred haptens include 5(6)-carboxyfluorescein, 2,4-dinitrophenyl, digoxigenin, and biotin.

Preferred fluorochromes (fluorophores) include 5(6)-carboxyfluorescein (Flu), 6-((7-amino-4-methylcoumarin-3-acetyl)amino)hexanoic acid (Cou), 5(and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.) or the Alexa dye series (Molecular Probes, Eugene, Oreg.).

Preferred enzymes include polymerases (e.g. Taq polymerase, Klenow PNA polymerase, T7 DNA polymerase, Sequenase, DNA polymerase 1 and phi29 polymerase), alkaline phosphatase (AP), horseradish peroxidase (HRP) and most preferably, soy bean peroxidase (SBP).

Detectable and Independently Detectable Moieties/ Multiplex Analysis

In preferred embodiments of this invention, a multiplex hybridization assay is performed. In a multiplex assay, numerous conditions of interest are simultaneously examined. Multiplex analysis relies on the ability to sort sample components or the data associated therewith, during or after the assay is completed. In preferred embodiments of the invention, one or more distinct independently detectable moieties are used to label two or more different probes used in an assay. The ability to differentiate between and/or quantitate each of the independently detectable moieties provides the means to multiplex a hybridization assay because the data which correlates with the hybridization of each of the distinctly (independently) labeled probe to a particular nucleic acid sequence can be correlated with the presence, absence or quantity of each organism sought to be detected in the sample. Consequently, the multiplex assays of this invention may be used to simultaneously detect the presence, absence or quantity of two or more organisms in the same sample and in the same assay.

Spacer/Linker Moieties

Generally, spacers are used to minimize the adverse effects that bulky labeling reagents might have on hybridization properties of probes. Linkers typically induce flexibility and randomness into the probe or otherwise link two or more nucleobase sequences of a probe or component polymer. Preferred spacer/linker moieties for the nucleobase polymers of this invention consist of one or more aminoalkyl carboxylic acids (e.g. aminocaproic acid) the side chain of an amino acid (e.g. the side chain of lysine or omithine) natural amino acids (e.g. glycine), aminooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3,6-dioxaoctane). Spacer/linker moieties may also incidentally or intentionally be constructed to improve the water solubility of the probe (For example see: Gildea et al., *Tett. Lett.* 39: 7255–7258 (1998)). Preferably, a spacer/linker moiety comprises one or more linked compounds having the formula: —Y—(O$_m$—(CW$_2$)$_n$)$_o$—Z—. The group Y is selected from the group consisting of: a single bond, —(CW$_2$)$_p$—, —C(O)(CW$_2$)$_p$—, —C(S)(CW$_2$)$_p$— and —S(O$_2$)(CW$_2$)$_p$. The group Z has the formula NH, NR$^2$, S or O. Each W is independently H, R$^2$, —OR$^2$, F, Cl, Br or I; wherein, each R$^2$ is independently selected from the group consisting of: —CX$_3$, —CX$_2$CX$_3$, —CX$_2$CX$_2$CX$_3$, —CX$_2$CX(CX$_3$)$_2$, and —C(CX$_3$)$_3$. Each X is independently H, F, Cl, Br or I. Each m is independently 0 or 1. Each n, o and p are independently integers from 0 to 10.

Hybridization Conditions/Stringency

Those of ordinary skill in the art of nucleic acid hybridization will recognize that factors commonly used to impose or control stringency of hybridization include formamnide concentration (or other chemical denaturant reagent), salt concentration (i.e., ionic strength), hybridization temperature, detergent concentration, pH and the presence or absence of chaotropes. Optimal stringency for a probe/target combination is often found by the well known technique of fixing several of the aforementioned stringency factors and then determining the effect of varying a single stringency factor. The same stringency factors can be modulated to thereby control the stringency of hybridization of a PNA to a nucleic acid, except that the hybridization of a PNA is fairly independent of ionic strength. Optimal stringency for an assay may be experimentally determined by examination of each stringency factor until the desired degree of discrimination is achieved.

Suitable Hybridization Conditions

Generally, the more closely related the background causing nucleic acid contaminates are to the target sequence, the more carefully stringency must be controlled. Blocking probes may also be used as a means to improve discrimination beyond the limits possible by mere optimization of stringency factors. Suitable hybridization conditions will thus comprise conditions under which the desired degree of discrimination is achieved such that an assay generates an accurate (within the tolerance desired for the assay) and reproducible result. Aided by no more than routine experimentation and the disclosure provided herein, those of skill in the art will easily be able to determine suitable hybridization conditions for performing assays utilizing the methods and compositions described herein. Suitable in-situ hybridization conditions comprise conditions suitable for performing an in-situ hybridization procedure. Thus, suitable in-situ hybridization conditions will become apparent using the disclosure provided herein; with or without additional routine experimentation.

Blocking Probes

Blocking probes are nucleic acid or non-nucleic acid probes which can be used to suppress the binding of the probing nucleobase sequence of the probing polymer to a non-target sequence. Preferred blocking probes are PNA probes (See: Coull et al., WIPO publication No. WO98/24933). Typically blocking probes are closely related to the probing nucleobase sequence and preferably they comprise a point mutation of the probing segment. It is believed that blocking probes operate by hybridization to the non-target sequence to thereby form a more thermodynamically stable complex than is formed by hybridization between the probing nucleobase sequence and the non-target sequence. Formation of the more stable and preferred complex blocks formation of the less stable non-preferred complex between the probing nucleobase sequence and the non-target sequence. Thus, blocking probes can be used with the methods, kits and compositions of this invention to suppress the binding of the nucleic acid or non-nucleic acid probe to a non-target sequence which might be present and interfere with the performance of the assay. Blocking probes are particularly advantageous in single point mutation discrimination.

Probing Nucleobase Sequence

The probing nucleobase sequence of a PNA probe is the specific sequence recognition portion of the construct. Therefore, the probing nucleobase sequence is a sequence of PNA subunits designed to hybridize to a target sequence wherein the presence, absence or amount of target sequence can be used to detect the presence, absence or number of organisms of interest in a sample. Consequently, with due consideration of the requirements of a PNA probe for the assay format chosen and the organism sought to be detected, the length of the probing nucleobase sequence of the PNA probe will generally be chosen such that a stable complex is formed with the target sequence under hybridization conditions or suitable in-situ hybridization conditions.

The probing nucleobase sequence suitable for detecting the target organism listed in the table, will generally, but not necessarily, have a length of 15 or fewer PNA subunits (most preferably 7–15 subunits in length) wherein the exact nucleobase sequence is at least 90% homologous to the probing nucleobase sequences listed in Table 1, or their complements. Longer probing nucleobase sequences may be used but they are not preferred. Complements of the probing nucleobase sequence are included since it is possible to prepare or amplify copies of the target sequence wherein the copies are complements of the target sequence and thus, will bind to the complement of the probing nucleobase sequences listed in Table 1. The most preferred 15-mer probing nucleobase sequences are listed in Table 1. These probing nucleobase sequences have been shown to be highly specific for the target organism in the presence of the other organisms listed in the table.

The probing nucleobase sequence of a PNA probe will generally have a probing nucleobase sequence which is complementary to the target sequence. Alternatively, a substantially complementary probing nucleobase sequence might be used since it has been demonstrated that greater sequence discrimination can be obtained when utilizing probes wherein there exists one or more point mutations (base mismatch) between the probe and the target sequence (See: Guo et al., *Nature Biotechnology* 15:331–335 (1997)).

This invention contemplates that variations in the probing nucleobase sequences listed in Table 1 shall provide PNA probes which are suitable for the specific detection of the organisms listed. Common variations include, deletions, insertions and frame shifts. Variation of the probing nucleobase sequences within the parameters described herein are considered to be an embodiment of this invention.

Probe Complexes

In still another embodiment, two probes are designed to hybridize to the target sequence sought to be detected to thereby generate a detectable signal whereby the probing nucleobase sequence of each probe comprises half or approximately half of the complete target sequence of the bacteria sought to be detected in the assay. As a non-limiting example, the probing nucleobase sequences of the two probes might be designed using the assay as described in European Patent Application 849,363, entitled "Method of identifying a nucleic acid using triple helix formation of adjacently annealed probes" by H. Orum et al. (See: EPA 849,363). Using this methodology, the probes which hybridize to the target sequence may or may not be labeled. However, it is the probe complex formed by the annealing of the adjacent probes which is detected. Similar compositions comprised solely of PNA probes have been described in copending and commonly owned application U.S. Ser. No. 09/302,238, herein incorporated by reference.

II. Preferred Embodiments of the Invention a. PNA Probes:

In one embodiment, this invention is directed to PNA probes. The PNA probes of this invention are suitable for detecting, identifying or quantitating one or more organisms of interest in a sample wherein the organisms are members of the bacterial species of *E. coli, Staphylococcus aureus, Pseudomonas aeruginosa, Pseudomonas cepatia, Pseudomonas fluorescens* or organisms of a bacterial genus including the Salmonella genus, Bacillus genus or Pseudomonas genus. General characteristics (e.g. length, labels, nucleobase sequences, linkers etc.) of PNA probes suitable for the detection, identification or quantitation of these specific microorganisms or bacteria of a genus have been previously described herein. The preferred probing nucleobase sequence of PNA probes of this invention are listed in Table 1.

TABLE 1

| Seq. ID No. | Probe Type | Target Organism | Probing Nucleobase Sequence |
|---|---|---|---|
| 1 | Species | E. coli | TCA-ATG-AGC-AAA-GGT |
| 2 | Species | S. aureus | GCT-TCT-CGT-CCG-TTC |
| 3 | Species | P. aeruginosa | CTG-AAT-CCA-GGA-GCA |
| 4 | | | AAC-TTG-CTG-AAC-CAC |
| 5 | Species | P. cepatia | CCA-TCG-CAT-CTA-ACA |

TABLE 1-continued

| Seq. ID No. | Probe Type | Target Organism | Probing Nucleobase Sequence |
|---|---|---|---|
| 6 | Species | P. fluorescens | TCT-AGT-CAG-TCA-GTT |
| 7 | Genus | Pseudomonas | GCT-GGC-CTA-GCC-TTC |
| 8 | | | GTC-CTC-CTT-GCG-GTT |
| 9 | | | TTC-TCA-TCC-GCT-CGA |
| 10 | Genus | Salmonella | CCG-ACT-TGA-CAG-ACC |
| 11 | | | CCT-GCC-AGT-TTC-GAA |
| 12 | Genus | Bacillus | CTT-TGT-TCT-GTC-CAT |

Note: The target sequence to which these probing nucleobase sequences hybridize have been analyzed using sequence alignment analysis of information currently in Genbank version 104. The alignment information indicates the sequences are specific to the target organisms listed.

However, the specificity of probes must be functionally examined since sequence alignment analysis does not always produce a target specific probe. The probing nucleobase sequences listed above have been determined to be organism specific by actual screening methods.

The PNA probes of this invention may comprise only a probing nucleobase sequence (as previously described herein) or may comprise additional moieties. Non-limiting examples of additional moieties include detectable moieties (labels), linkers, spacers, natural or non-natural amino acids, or other subunits of PNA, DNA or RNA. Additional moieties may be functional or non-functional in an assay. Generally however, additional moieties will be selected to be functional within the design of the assay in which the PNA probe is to be used. The preferred PNA probes of this invention are labeled with one or more detectable moieties. In a more preferred embodiment, one or more probes are labeled with two or more independently detectable moieties. Preferred independently detectable moieties are independently detectable fluorophores.

In preferred embodiments, the probes of this invention are used in in-situ hybridization (ISH) and fluorescence in-situ hybridization (FISH) assays. Excess probe used in a ISH or FISH assay typically must be removed so that the detectable moiety of specifically bound probes can be detected above the background signal which results from still present but unhybridized probe. Generally the excess probe is washed away after the sample has been incubated with probe for a period of time. However, use of dark probes are a preferred embodiment of this invention, since there is no requirement that excess dark probe be completely removed (washed away) from the sample since it generates little or no detectable background.

As used herein, a "dark probe" shall be a PNA probe which hybridizes to a nucleic acid target to thereby cause a detectable change in at least one physical property of at least one attached label in a manner which can be used to detect, identify or quantitate the presence of an organism of interest in a sample of interest. Non-limiting examples of dark probes include PNA Molecular Beacons (See: WO99/21881 and U.S. Ser. No. 08/958,532 (abandoned) and copending and commonly owned U.S. Ser. No. 09/179,298, both incorporated herein by reference) as well as Linear Beacons (See: WO99/22018 and copending and commonly owned U.S. Ser. No. 09/179,162, herein incorporated by reference). Thus, changes in signal in the assay utilizing a "dark probe" can be directly correlated with hybridization of the probing nucleobase sequence to the target sequence of a bacteria of interest.

Unlabeled Non-Nucleic Acid Probes

The probes of this invention need not be labeled with a detectable moiety to be operable within the method of this invention. When using the probes of this invention it is possible to detect the probe/target sequence complex formed by hybridization of the probing nucleobase sequence of the probe to the target sequence. For example, a PNA/nucleic acid complex formed by the hybridization of a PNA probing nucleobase sequence to the target sequence could be detected using an antibody which specifically interacts with the complex under antibody binding conditions. Suitable antibodies to PNA/nucleic acid complexes and methods for preparation and use are described in WIPO Patent Application WO95/17430 and U.S. Pat. No. 5,612,458, herein incorporated by reference.

The antibody/PNA/nucleic acid complex formed by interaction of the α-PNA/nucleic acid antibody with the PNA/nucleic acid complex can be detected by several methods. For example, the α-PNA/nucleic acid antibody could be labeled with a detectable moiety such as an enzyme. Suitable detectable moieties have been previously described herein. Thus, the presence, absence or quantity of the detectable moiety is correlated with the presence, absence or quantity of the antibody/PNA/nucleic acid complex and the organism to be identified by the probing nucleobase sequence of the PNA probe. Alternatively, the antibody/PNA/nucleic acid complex is detected using a secondary antibody which is labeled with a detectable moiety. Typically the secondary antibody specifically binds to the (x-PNA/nucleic acid antibody under antibody binding conditions. Thus, the presence, absence or quantity of the detectable moiety is correlated with the presence, absence or quantity of the antibody/antibody/PNA/nucleic acid complex and the organism to be identified by the probing nucleobase sequence of the probe. As used herein, the term antibody shall include antibody fragments which specifically bind to other antibodies or other antibody fragments.

Advantages of Using PNA Probes

Fuchs et al. (*Applied and Environmental Microbiology*, 64: 4973–4982 (1998)) have demonstrated that the ability of nucleic acid probes to hybridize to target sequences of rRNA (e.g. targets like 16S or 23S rRNA) is highly dependent upon whether the site of hybridization is placed in or outside the highly structured helix regions. Moving the probe just a few bases in or out of such a structured region can give rise to significant changes in the overall signal intensity. The lack of signal intensity is believed to result from the lack of probe accessibility to the hybridization site within the secondary structure.

When designing species specific nucleic acid probes, nucleobase sequence selection is further limnited because rRNA is relatively well conserved between related species. Moreover, the limited number of species specific sequence variations are often concentrated in the highly structured regions of the rRNA. Therefore, some of the most useful regions of diverse nucleobase sequences suitable for designing species specific probes are often unavailable to nucleic acid probes.

Because of its unique structure, PNA probes can be designed to target highly structured regions of rRNA. Thus, PNA probes do not suffer from the limitations characteristic for nucleic acid probes. For example, Salmonella 16S rRNA is less than 4% different as compared with *E. coli* 16S rRNA. However, in the highly structured helix #18 there exists a significant number of differences (i.e. 14 nucleobase differences over a stretch of 26 nucleobases). This region would therefore be a fertile source of variable sequence with which to attempt to design probes capable of distinguishing between these two species. However, as reported by Fuchs et al., DNA probes directed to this particular highly structured region (Eco455 and Eco468 in Table 1 of Fuchs et al.) generated only a small fraction (i.e. 3%) of the signal which was obtained with the best DNA probe (Eco1482 in Table 1 of Fuchs et al.). By comparison, a PNA probe directed to this structured region (Probing Nucleobase Sequence 1 described in Table 1 of this invention) functions well as determined by the signal obtained in FIG. 3.

b. PNA Probe Sets:

In another embodiment, this invention is directed to a PNA probe set suitable for detecting, identifying or quantitating one or more organisms of interest in a sample wherein the organisms are members of the bacterial species of *E. coli, Staphylococcus aureus, Pseudomonas aeruginosa, Pseudomonas cepatia, Pseudomonas fluorescens* or organisms of a bacterial genus including the Salmonella genus, Bacillus genus or Pseudomonas genus. The general and preferred characteristics of PNA probes suitable for the detection, identification or quantitation of these specific microorganisms or bacteria of a genus have been previously described herein. Preferred probing nucleobase sequences are listed in Table 1. The grouping of PNA probes within sets characterized for specific groups of organisms (e.g. classification within species or genus, etc.) is contemplated as a preferred embodiment of this invention. Probe sets of this invention shall comprise at least one PNA probe but need not comprise only PNA probes. For example, probe sets of this invention may comprise mixtures of PNA probes and nucleic acid probes, provided however that a set comprises at least one PNA probe as described herein. In preferred embodiments, some of the probes of the set are blocking probes composed of PNA or nucleic acid but preferably the blocking probes are PNA.

Table 1 lists several species or genus of bacteria for which two or more probing nucleobase sequences can be used to detect the target organism. Where alternative probing nucleobase sequences exist, it is preferable to use a probe set containing the two or more PNA probes to thereby increase the detectable signal in the assay.

One exemplary probe set would comprise probes suitable for the detection of one or more bacterial species consisting of at least *E. coli, Staphylococcus aureus, Pseudomonas aeruginosa, Pseudomonas cepatia* and *Pseudomonas fluorescens*. A suitable probe set would contain at least one, and preferably all, of the following PNA probes. At least one PNA probe suitable for detecting *E. coli* and having a probing nucleobase sequence TCA-ATG-AGC-AAA-GGT (Seq. ID NO.2). At least one PNA probe suitable for detecting *Staphylococcus aureus* and having a probing nucleobase sequence GCT-TCT-CGT-CCG-TTC Seq. ID No.2. At least one PNA probe suitable for detecting *Pseudomonas aeruginosa* and having a probing nucleobase sequence selected from the group consisting of CTG-AAT-CCA-GGA-GCA Seq. ID No.3 and AAC-TTG-CTG-AAC-CAC Seq. ID No.4. At least one PNA probe suitable for detecting. *Pseudomonas cepatia* and having a probing nucleobase sequence CCA-TCG-CAT-CTA-ACA Seq. ID No.5. At least one PNA probe suitable for detecting *Pseudomonas fluorescens* and having a probing nucleobase sequence TCT-AGT-CAG-TCA-GTT Seq. ID No.6. As previously suggested, the probe set may contain other nucleic acid or PNA probes directed to other target organisms or as blocking probes.

A second exemplary probe set would comprise probes suitable for the detection of one or more bacteria of a genus consisting of at least the Salmonella genus, Bacillus genus or Pseudomonas genus. A suitable probe set would contain at least one, and preferably all, of the following PNA probes. At least one PNA probe suitable for detecting bacteria of the Salmonella genus and having a probing nucleobase sequence selected from the group consisting of CCG-ACT-TGA-CAG-ACC Seq. ID No.10 and CCT-GCC-AGT-TTC-GAA Seq. ID No.11. At least one PNA probe suitable for detecting bacteria of the Bacillus genus and having a probing nucleobase sequence CTT-TGT-TCT-GTC-CAT Seq. ID No.12. At least one PNA probe suitable for detecting bacteria of the Pseudomonas genus and having a probing nucleobase sequence selected from the group consisting of GCTG-GC-CTA-GCC-TTC Seq. ID No.7, GTC-CTC-CTT-GCG-GTT Seq. ID No.8 and TTC-TCA-TCC-GCT-CGA Seq. ID No.9. The three aforementioned PNA probing nucleobase sequences have been found to be suitable for specifically detecting bacteria of the Pseudomonas genus including *Pseudomonas aeruginosa, Pseudomonas cepatia, Pseudomonas fluorescens* and *Pseudomonas putida*. As previously suggested, the probe set may contain other nucleic acid or PNA probes directed to other target organisms or as blocking probes.

The detection, identification or quantitation of certain organisms is particularly useful where these organisms comprise a group of pathogens for which a contamination limit applies by industry standard or by governmental regulation. One such group of organisms are the bacterial pathogens of the United States Pharmacopoeia (USP bacteria). USP bacteria include *E. coli*, the Salmonella genus, *Pseudomonas aeruginosa* and *Staphylococcus aureus*. Food, beverage and pharmaceutical products are routinely examined for the presence, absence or number of these USP bacteria. Consequently, a set of PNA probes suitable for the detection of the USP bacteria is a preferred embodiment of this invention.

The probing nucleobase sequences of PNA probes suitable for the detection of USP bacteria have been previously listed in Table 1. Most preferably, this set of PNA probes is suitable for the detection of all of the USP bacteria. An exemplary probe set would contain at least one, and preferably all, of the following PNA probes. A PNA probe suitable for detecting *E. coli* and having a probing nucleobase sequence TCA-ATG-AGC-AAA-GGT Seq. ID No.1. At least one PNA probe suitable for detecting Salmonella and having a probing nucleobase sequence selected from the group consisting of CCG-ACT-TGA-CAG-ACC Seq. ID No.10 and CCT-GCC-AGT-TTC-GAA Seq. ID No.11. At least one PNA probe suitable for detecting *Pseudomonas aeruginosa* and having a probing nucleobase sequence selected from the group consisting of CTG-AAT-CCA-GGA-GCA Seq. ID No.3 and AAC-TTG-CTG-AAC-CAC Seq. ID No.4. A PNA probe suitable for detecting *Staphylococcus aureus* and having a probing nucleobase sequence GCT-TCT-CGT-CCG-TTC Seq. ID No.2. As previously suggested, the probe set may contain other nucleic acid or PNA probes directed to other target organisms or as blocking probes.

c. Methods:

In another embodiment, this invention is directed to a method suitable for detecting, identifying or quantitating one or more organisms of interest in a sample wherein the organisms are members of the bacterial species of *E. coli, Staphylococcus aureus, Pseudomonas aeruginosa, Pseudomonas cepatia, Pseudomonas fluorescens* or organisms of a bacterial genus including the Salmonella genus, Bacillus genus or Pseudomonas genus. The general and preferred characteristics of PNA probes suitable for the detection, identification or quantitation of these target organisms have been previously described herein. Preferred probing nucleobase sequences are listed in Table 1.

The method comprises contacting the sample with one or more PNA probes, wherein suitable probes have been previously described herein. According to the method, the presence, absence or number of the one or more organisms of interest in the sample are then detected, identified or quantitated by correlating hybridization of the probing nucleobase sequence of a PNA probe to the target sequence of a target organism under suitable hybridization conditions or suitable in-situ hybridization conditions.

The grouping of PNA probes within probe sets to be used with methods for detecting specific groups of organisms (e.g. classification within species, genus or USP bacteria) is contemplated as a preferred embodiment of this invention. Exemplary probes and probe sets suitable for the practice of this method have been previously described herein.

Exemplary Media Based Analysis of Bacteria

The methods, kits and compositions of this invention are particularly useful for the rapid probe-based detection, identification and quantitation of viable bacteria. For example, it is possible to use of enzyme-linked PNA probes in combination with in-situ analysis of microcolonies of bacteria grown (using selective media) directly on the medium on which they were isolated from the sample (i.e. a filtration membrane) to thereby achieve the rapid, sensitive and specific analysis of bacteria in a manner which was not previously possible.

The rapid probe-based analysis of growing bacteria requires very high sensitivity in addition to probe specificity because the cell count is limited during the early stages of cell division. Since probe-based analysis detects nucleic acid, the analysis of growing bacteria is used to distinguish between viable organisms and dead (non-viable) organisms, the presence of which are not considered to cause food or beverage spoilage or contamination.

Enzyme-linked probes are preferred for such rapid analysis since the enzymes can rapidly and repetitively turn over a substrate to thereby achieve signal amplification suitable for high sensitivity detection. Preferred, non-limiting, substrates include chemiluminescent compounds, fluorophores and chromophores. PNA probes are the preferred probe type since they hybridize rapidly to nucleic acid and are generally more specific than nucleic acid probes. Furthermore, PNA probes operate under conditions of low ionic strength (favored conditions for hybridizing to structured rRNA) and they form very stable hybrids. In-situ analysis is preferred since viability of colony forming units (CFU) can be absolutely determined and optionally quantitated by scoring the colonies observed.

In preferred embodiments, the bacteria are grown directly on an isolation medium. Integration of the isolation medium with the growth of the bacteria eliminates the need for a transfer pre- and post-culture growth and thereby eliminates the opportunity for error associated therewith. Preferably, the isolation medium is a filter or a membrane filter. Preferred filters are microporous membrane filters such as those sold by Millipore Corporation for the filtration of liquids. Pore sizes of the filter are generally chosen so that the bacteria will not pass though the pores thereby insuring that all the bacteria in the sample is collected on the filter.

Once the sample is collected on the isolation medium, the bacteria are grown in a manner specific for the organism or organisms of interest using methods known in the art.

Preferably, the culture is grown using a selective culture media. By "selective culture media" we mean a culture media which will support the specific growth of the organism or organisms of interest while inhibiting the growth of non-target organisms which might cause non-specific signal in the assay. For example, Applicants are aware of certain organisms having endogenous peroxidase activity which will generate signal, in the presence of the chemiluminescent substrate used in the assay.

After the bacteria are grown, typically they are fixed. Cell fixation is a term well known in the art of in-situ hybridization and is generally, but not necessarily, part of the in-situ hybridization process.

Using probe-based in-situ analysis of the isolation medium after organism growth, the number of colony forming units (CFU) of bacteria which are detected by the organism specific probe, can be counted or scored (manually or by automated methods) after an appropriate incubation period. Because the bacteria grow rapidly and the enzyme-linked PNA probes are suitable for high sensitivity analysis, typically, the assay can be performed in 1–4 hours. Because the bacterial are preferably grown directly on the isolation medium, the colonies detected are each representative of a colony forming unit (CFU) isolated from the sample. Since the volume of sample filtered to isolate the bacteria is known and since only viable organisms grow, the CFU's per unit volume of sample can be directly determined.

d. Kits:

In yet another embodiment, this invention is directed to kits suitable for performing an assay which detects the presence, absence or number of one or more target organisms in a sample. Target organisms include members of the bacterial species of *E. coli, Staphylococcus aureus, Pseudomonas aeruginosa, Pseudomonas cepatia, Pseudomonas fluorescens* or organisms of a bacterial genus including the Salmonella genus, Bacillus genus or Pseudomonas genus. The general and preferred characteristics of PNA probes suitable for the detection, identification or quantitation of these target organisms have been previously described herein. Preferred probing nucleobase sequences are listed in Table 1. Furthermore, methods suitable for using the PNA probes or PNA probes sets of a kit to detect, identify or quantitate target organisms in a sample of interest have been previously described herein.

The kits of this invention comprise one or more PNA probes and other reagents or compositions which are selected to perform an assay or otherwise simplify the performance of an assay. Preferred kits of the invention will be prepared for detecting specific groups of organisms (e.g. classification within species, genus or USP organisms). In kits which contain sets of probes, wherein each of at least two probes of the set are used to detect different target organisms, the probes of the set are preferably labeled with one or more independently detectable moieties so that each specific target organism can be individually detected, identified or quantitated in a single assay.

Exemplary Assay Formats

The probes, probe sets, methods and kits of this invention are suitable for the detection, identification or quantitation of bacteria of certain genus or species. In preferred embodiments, in-situ hybridization is used as the assay format for detecting identifying or quantitating target organisms. Most preferably, fluorescence in-situ hybridization (FISH or PNA-FISH) is the assay format. Exemplary methods for performing PNA-FISH can be found in: Thisted et al. Cell Vision, 3:358–363 (1996) or WIPO Patent Application WO97/18325, herein incorporated by reference, as well as the Examples of this specification.

Methods used to experimentally test specific PNA probes in PNA-FISH assays can be found in Examples 9 and 10 of this specification. The examples contained herein demonstrate that labeled PNA probes comprising the probing nucleobase sequences listed in Table 1 are highly specific for detecting target organisms even when other organisms listed in the table are present in the assay. The experimental conditions used in the Examples yield results within approximately 1–4 hours. The identical experimental protocol was found to be sensitive, reliable and generally applicable regardless of the nature or sequence of the PNA probes used.

Organisms which have been treated with the probes, probe sets or probes contained in the kits of this invention can be detected by several exemplary methods. The cells can be fixed on slides or visualized with a film, camera, microscope (See for example: Examples 9 and 10 contained herein) or laser scanning device. Alternatively, the cells can be fixed and then analyzed in a flow cytometer (See for example: Lansdorp et al.; WIPO Patent Application; WO97/14026). Slide scanners and flow cytometers are particularly useful for rapidly quantitating the number of target organisms present in a sample of interest.

Exemplary Multiplex PNA-FISH Assays

Because the PNA probes of this invention can be labeled with one or more independently detectable moieties, it is possible to design PNA probe sets wherein each probe of the set is independently detectable. Fluorophores which have sufficiently different excitation and emission spectra are often used as independently detectable moieties. Exemplary independently detectable fluorophores are derivatives of coumarin, fluorescein and rhodamine such as those used in Examples 9 and 10 of this specification. Thus, an assay wherein a PNA probe set comprising three PNA probes, each labeled with one of an independently detectable derivative of coumarin, fluorescein or rhodamine, could be used to independently detect, identify or quantitate, in the same assay, each of three different organisms which might be present in a sample of interest. Consequently, the PNA probes, PNA probe sets, methods and kits of this invention are particularly useful for the rapid, sensitive, reliable and versatile multiplex analysis of two or more organisms in a single sample or assay. By versatile we mean that the method is generally applicable despite substantial variability in the nucleobase sequences of the probes used in the assay.

The rational described above for performing multiplex assays can be further extended. For example, any three independently detectable moieties can be used to detect, identify or quantitate more than three different organisms of interest provided certain of the probes of a set can be labeled with two or more independently detectable moieties. Several alternative methods for labeling PNAs have been previously referred to herein. Judicious choice of labeling reagents and labeling methodologies can be used to introduce multiple independently detectable moieties into a single PNA probe.

Table 2 lists probes of an exemplary PNA probe set which could be used to independently detect 5 species of bacteria and the Salmonella genus in a single assay. As illustrated in the table, each of the PNA probes used to detect the *Pseudomonas aeruginosa, Pseudomonas cepatia* and *Pseudomonas fluorescens* species could be labeled with only one of the three fluorophores whereas the PNA probes for detection of the *E. coli, Staphylococcus aureus* species and bacteria of the Salmonella genus could be labeled with each of two of the fluorophores wherein the combination of the two fluorophores is unique to each PNA probe. Using this configuration of labeled PNA probes, all of the bacteria listed in Table 2 can be independently detected, identified or quantitated since each organism of interest will correlate with a unique independently detectable fluorophore or combination of two independently detectable fluorophores. For example, *Pseudomonas aeruginosa* will exhibit a blue signal whereas *E. coli* will exhibit both a blue and green signal.

TABLE 2

| Target Organism | Fluorophore Linked To Probe For Detecting Target Organism | Independently Detectable Visible Color(s) |
| --- | --- | --- |
| P. aeruginosa | Coumarin | Blue |
| P. cepatia | Fluorescein | Green |
| P. fluorescens | Rhodamine | Red |
| E. Coli | Coumarin and Fluorescein | Blue and Green |
| S. aureus | Coumarin and Rhodamine | Blue and Red |
| Salmonella | Fluorescein and Rhodamine | Green and Red |

Example 10 of this specification demonstrates the feasibility of multiplex fluorescent in-situ hybridization using independently detectable PNA probes wherein at least one probe of the set is labeled with two fluorochrome moieties. In this example, all four USP bacteria are individually detectable in an assay format which allows individual cells to be counted. Thus, it has been demonstrated that a single assay can be used to detect, identify and quantitate *E. coli*, Salmonella, *Pseudomonas aeruginosa* and *Staphylococcus aureus* (the USP bacteria) present in a single sample using three fluorescent dyes. This assay can be performed in approximately 3 hours and allows for the sensitive detection, identification and/or quantitation of each of the USP bacteria.

Those of ordinary skill in the art will recognize that this method for increasing the number of organisms which can be independently detected in a single assay (multiplex analysis) is limited only by the number of independently detectable moieties available for use in the assay format and the number of independently detectable moieties which can be linked to the probes used in the assay. Thus, this invention contemplates assays wherein tens or even hundreds of organisms of interest can be simultaneous detected, identified or quantitated.

Immobilization of Probes To A Surface

One or more of the PNA probes of this invention may optionally be immobilized to a surface for the detection of the target sequence of a target organism of interest. PNA probes can be immobilized to the surface using the well known process of TV-crosslinking. More preferably, the PNA probe is synthesized on the surface in a manner suitable for deprotection but not cleavage from the synthesis support (See: Weiler, J. et al, Hybridization based DNA screening on peptide nucleic acid (PNA) oligomer arrays., Nucl. Acids Res., 25, 14:2792–2799 (July 1997)). In still another embodiment, one or more PNA probes are covalently linked to a surface by the reaction of a suitable functional group on the probe with a functional group of the surface (See: Lester, A. et al, "PNA Array Technology": Presented at Biochip Technologies Conference in Annapolis (October 1997)). This method is most preferred since the PNA probes on the surface will typically be highly purified and attached using a defined chemistry, thereby mininizing or eliminating non-specific interactions.

Methods for the chemical attachment of probes to surfaces generally involve the reaction of a nucleophilic group, (e.g. an amine or thiol) of the probe to be immobilized, with an electrophilic group on the support to be modified. Alternatively, the nucleophile can be present on the support and the electrophile (e.g. activated carboxylic acid) present on the probe. Because native PNA possesses an amino terminus, a PNA will not necessarily require modification to thereby immobilize it to a surface (See: Lester et al., Poster entitled "PNA Array Technology").

Conditions suitable for the immobilization of a PNA probe to a surface will generally be similar to those conditions suitable for the labeling of the polymer. The immobilization reaction is essentially the equivalent of labeling whereby the label is substituted with the surface to which the polymer is to be linked.

Numerous types of surfaces derivatized with amino groups, carboxylic acid groups, isocyantes, isothiocyanates and malimide groups are commercially available. Non-limiting examples of suitable surfaces include membranes, glass, controlled pore glass, polystyrene particles (beads), silica and gold nanoparticles.

Arrays of PNA Probes or Probe Sets

Arrays are surfaces to which two or more probes have been immobilized each at a specified position. Typically, the probing nucleobase sequence of the immobilized probes is judiciously chosen to interrogate a sample which may contain one or more target organisms. Because the location and composition of each immobilized probe is known, arrays are generally useful for the simultaneously detection, identification or quantitation of two or more target organisms which may be present in the sample. Moreover, arrays of PNA probes may be regenerated by stripping the hybridized nucleic acid after each assay, thereby providing a means to repetitively analyze numerous samples using the same array. Thus, arrays of PNA probes or PNA probe sets may be useful for repetitive screening of samples for target organisms of interest. The arrays of this invention comprise at least one PNA probe (as described herein) suitable for the detection, identification or quantitationr of at least one target organism (as described herein). Preferred probing nucleobase sequences for the immobilized PNA probes are listed in Table 1.

Exemplary Applications for Using the Invention

Whether support bound or in solution, the PNA probes, probe sets, methods and kits of this invention are particularly useful for the rapid, sensitive and reliable detection of bacteria (pathogens) in food, beverages, water, pharmaceutical products, personal care products, dairy products or environmental samples. The analysis of preferred beverages include soda, bottled water, fruit juice, beer, wine or liquor products. Suitable PNA probes, probe sets, methods and kits will be particularly useful for the analysis of raw materials, equipment, products or processes used to manufacture or store food, beverages, water, pharmaceutical products, personal care products, dairy products or environmental samples.

Whether support bound or in solution, the PNA probes, probe sets, methods and kits of this invention are also particularly useful for the rapid, sensitive and reliable detection of bacteria (pathogens) in clinical environments. Suitable PNA probes, probe sets, methods and kits will be particularly useful for the analysis of clinical specimens, equipment, fixtures or products used to treat humans or animals.

Having described the preferred embodiments of the invention, it will now become apparent to one of skill in the art that other embodiments incorporating the concepts described herein may be used. It is felt, therefore, that these embodiments should not be limited to disclosed embodiments but rather should be limited only by the spirit and scope of the following claims.

EXAMPLES

This invention is now illustrated by the following examples which are not intended to be limiting in any way.

Example 1

Synthesis of bis-(2-Methoxyethyl)amidyl-diglycolic Acid

To 500 mmol of diglycolic anhydride stirring in 800 mL of dichloromethane (DCM) was added dropwise, 1.1 mole of bis(2-methoxyethyl)amine (Aldrich Chemical). The reaction was allowed to stir for 2 hours and then 280 mL of 6N HCl was added dropwise. The contents were then transferred to a separatory funnel and allowed to separate. The DCM layer was removed and the aqueous layer extracted with 100 mL of DCM. The combined DCM layers were then extracted with 100 mL of 10% aqueous citric acid. The DCM layer was then separated, dried ($Na_2SO_4$), filtered and evaporated to yield 73.8 g (296 mmole; 59% yield). A kugelrorh was then used to remove traces of solvent (product was heated to 60° C. at approximately 180 $\mu$M Hg).

Example 2

Synthesis of N-[N"-Fmoc-(2"-Aminoethyl)]-N-[N, N'-(2-methoxyethyl)amidyl-diglycolyl]glycine ("Fmoc-" E "aeg-OH")

To 60 mmol of Fmoc-aeg-OH (PE Biosystems, Foster City, Calif. Biosystems, Inc.) was added 360 mL of MilliQ water, 180 mL of acetone, 120 mmol of $NaHCO_3$ and 60 mmol of $K_2CO_3$. This solution was allowed to stir until all the Fmoc-aeg-OH had dissolved (approx. 2 hr.) and then the solution prepared, as described below, was added.

To 70 mmol of bis-(2-methoxyethyl)amidyl-diglycolic acid was added 120 mL of anhydrous acetonitrile (Fluka Chemical), 240 mmol of N-methylmorpholine (NMM; Fluka Chemical) and 75 mmol of trimethylacetyl chloride (Aldrich Chemical). The solution was allowed to stir at room temperature for 30 minutes and then added dropwise to the solution of Fmoc-aeg-OH which was prepared as described above.

After the combined solutions stirred for 1 hr and tlc analysis indicated complete reaction, 6N HCl was added to the reaction until the pH was less than 2 by paper. The organic solvent was then removed by vacuum evaporation. The remaining aqueous solution was then transferred to a separatory funnel and extracted 2× with 250 mL of ethyl acetate. The combined ethyl acetate layers were dried ($Na_2SO_4$), filtered and evaporated to yield 41.5 g of an oil.

This crude product was purified by column chromatography using a reversed phase stationary phase (C18) and a gradient of aqueous acetonitrile to elute the product and remove the pivalic acid. Though not visible by tlc, the elution of the pivalic acid can be monitored by smell. The pivalic acid can be almost completely eluted from the column prior to elution of the product. Elution of the product can be monitored by tlc. Yield 26.8 g (47 mmol; 78%). An "E" modification of a PNA or polyamide has the formula:

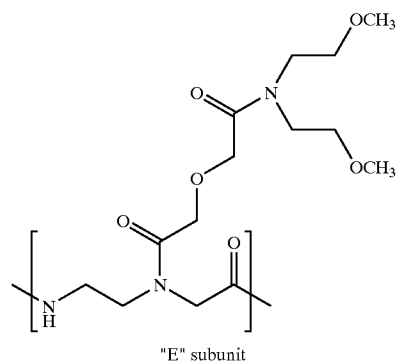

"E" subunit

Example 3

Synthesis of PNAs

Unless, otherwise stated, PNAs were synthesized using commercially available reagents and instrumentation obtained from PE Biosystems, Foster City, Calif. USA. PNAs possessing C-terminal modifications were prepared by performing the synthesis using prederivatized synthesis support or by performing the synthesis using the Fmoc-K (Mtt)-OH (Bachem, Torrance, Calif., USA, P/N B-2535) or Fmoc-"E"aeg-OH (prepared as described above) monomers.

Example 4

Preferred Method for Removal of the Fmoc Protecting Group

The synthesis support was treated with a solution of 25% piperidine in DMF for 10–15 minutes at room temperature. After treatment, the synthesis support was washed and dried under high vacuum. The support can the be treated with labeling reagent (See: Example 6).

Example 5

Preferred Method for Removal of the Mtt Protecting Group From Lysine (K)

The resin (still in the synthesis column) was treated with 10 mL of a solution containing 1% trifluoroacetic acid, 5% triisopropylsilane (TIS) in dichloromethane by passing the solution through the column over a period of approximately 15 minutes. After treatment, the synthesis support was washed with DMF. Prior to treatment with labeling reagent (See: Example 6), the support was neutralized by treatment with approximately 10 mL of a solution containing 5% diisopropylethylamine in DMF.

Note: This procedure was only performed on PNA prepared using Fmoc-PAL-PEG/PS (PE Biosystems, Foster City, Calif. P/N GEN913384). It was not performed with Fmoc-XAL-PEG/PS (PE Biosystems, Foster City, Calif. P/N GEN913394).

Example 6

Preferred Method for Amine Labeling of Support Bound PNA with the NHS Esters of 5(6) carboxyfluorescein (Flu) 6-((7-Amino-4-methylcoumarin-3-acetyl)amino)hexanoic Acid (Cou) or 5(and 6)-carboxy-X-rhodamine (Rox)

The amino protecting group (Fmoc or Mtt) of the assembled PNA was removed and the synthesis support was washed and dried under vacuum. The synthesis support was then treated for 4–5 hours at 30–37° C. with approximately 250 μL of a solution containing 0.08 M NHS ester labeling reagent, 0.24 M DIEA and 0.24 M 2,6-lutidine. After treatment the synthesis support was washed and dried under high vacuum. The PNA oligomer was then cleaved, deprotected and purified.

The PNA labeled with both Rox and Flu (Flu-Rox-1: Table 3) was first treated to remove the Fmoc group. The support was then treated with the Flu-NHS ester. Next the Mtt group was removed and the support was then treated with the Rox-NHS ester. The PNA was then cleaved from the synthesis support, deprotected and purified.

Example 7

General Procedure for Cleavage, Deprotection and Purification

The synthesis support (Fmoc-PAL-PEG/PS; P/N GEN913384) was then removed from the synthesis cartridge, transferred to a Ultrafree spin cartridge (Millipore Corp., P/N SE3P230J3) and treated with a solution of TFA/m-cresol (either of 7/3 or 8/2 (preferred)) for 1–3 hours. The solution was spun through the support bed and again the support was treated with a solution of TFA/m-cresol for 1–3 hours. The solution was again spun through the support bed. The combined eluents (TFA/m-cresol) was then precipitated by addition of approximately 1 mL of diethyl ether. The precipitate was pelletized by centrifugation. The pellet was then resuspended in ethyl ether and pelletized two additional times. The dried pellet was then resuspended in 20% aqueous acetonitrile (ACN) containing 0.1% TFA (additional ACN was added as necessary to dissolve the pellet). The product was analyzed and purified using reversed phase chromatographic methods.

Note: Several PNAs were prepared using new product Fmoc-XAL-PEG/PS synthesis support (P/N GEN 913394) available from PE Biosystems, Foster City, Calif. This support has the advantage that the PNA can be removed more rapidly and under more mildly acid conditions. For PNAs prepared with Fmoc-XAL-PEG/PS the support is treated as described above except that a solution of TFA/m-cresol 9/1 was used for a period of 10–15 minutes (2×).
PNA Oligomers Prepared:

TABLE 3

| Probe ID | Target Organism | PNA Probe Sequence |
| --- | --- | --- |
| Flu-1 | E. coli | Flu-OO-TCA-ATG-AGC-AAA-GGT-NH$_2$ |
| Flu-2 | S. aureus | Flu-OO-GCT-TCT-CGT-CCG-TTC-NH$_2$ |
| Flu-3 | P aeruginosa | Flu-OO-CTG-AAT-CCA-GGA-GCA-NH$_2$ |
| Flu-4 | P aeruginosa | Flu-OO-AAC-TTG-CTG-AAC-CAC-NH$_2$ |
| Flu-5 | P. cepatia | Flu-OO-CCA-TCG-CAT-CTA-ACA-NH$_2$ |
| Flu-6 | P. fluorescens | Flu-OO-TCT-AGT-CAG-TCA-GTT-NH$_2$ |
| Flu-7 | Pseudomonas genus | Flu-OO-GCT-GGC-CTA-GCC-TTC-NH$_2$ |
| Flu-8 | Pseudomonas genus | Flu-OO-GTC-CTC-CTT-GCG-GTT-NH$_2$ |
| Flu-9 | Pseudomonas genus | Flu-OO-TTC-TCA-TCC-GCT-CGA-NH$_2$ |
| Flu-10 | Salmonella genus | Flu-OO-CCG-ACT-TGA-CAG-ACC-NH$_2$ |
| Flu-11 | Salmonella genus | Flu-OO-CCT-GCC-AGT-TTC-GAA-NH$_2$ |
| Flu-12 | Bacillus genus | Flu-OO-CTT-TGT-TCT-GTC-CAT-NH$_2$ |
| Cou-10 | Salmonella genus | Cou-OO-CCG-ACT-TGA-CAG-ACC-NH$_2$ |

TABLE 3-continued

| Probe ID | Target Organism | PNA Probe Sequence |
| --- | --- | --- |
| Rox-2 | S. aureus | Rox-OO-GCT-TCT-CGT-CCG-TTC-NH$_2$ |
| Flu-Rox-1 | E. Coli | Flu-OO-TCA-ATG-AGC-AAA-GGT-EE-OK(Rox)-NH$_2$ |

All PNA sequences are written from the amine (N-) terminus to the carboxyl (C-) terminus. Flu=5(6)-carboxyfluorescein, Cou=6-((7-amino-4-methylcoumarin-3-acetyl)amino)hexanoic acid; Rox=5(and 6)-carboxy-X-rhodamine; E is defined above; O=8-amino-3,6-dioxaoctanoic acid; and K=the amino acid L-Lysine.

Example 8

Dot Blot rRNA Preparation:
Using a Qiagen kit (P/N 75144), total RNA (including app. 80% rRNA) was isolated It from the different bacteria which had been grown in culture. The amount of RNA isolated was determined by measuring the absorption at 260 nm.

Hybridization to the Membranes:
Dot blots were made on nylon membranes obtained from Gibco-BRL (P/N 14830-012). For the RNA of each cultured bacteria, a dilution row containing 5 spots was made, starting with a concentration of 16 mM RNA for the strongest solution and continuing with half log dilutions in diethyl pyrocarbonate (DEPC) treated water (RNase free). Prior to spotting on the membrane, each dilution stock was heated to 68° C. for three minutes. The spotting produced a half log dilution series containing approximately 16, 5.1, 1.6, 0.52, and 0.17 ng total RNA per spot. Once the spots had air dried, the membrane was UV-crosslinked and then stored in a plastic bag until used.

Figure 2:
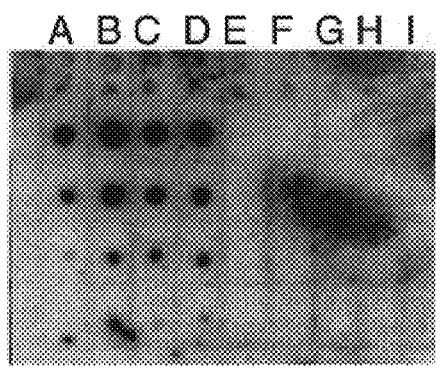
FIGS. 2-I through 2-IV are electronic images of dot blot assays used to examine the specificity of PNA oligomers for certain target organisms of a bacterial genus.
Figure 2:
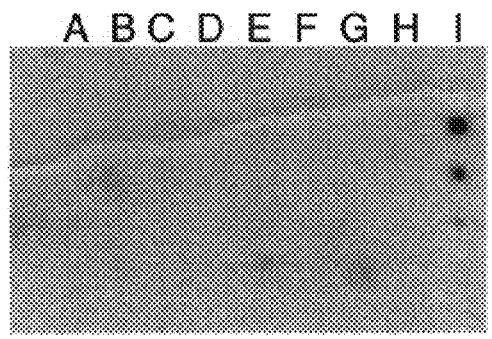
Figure 2:
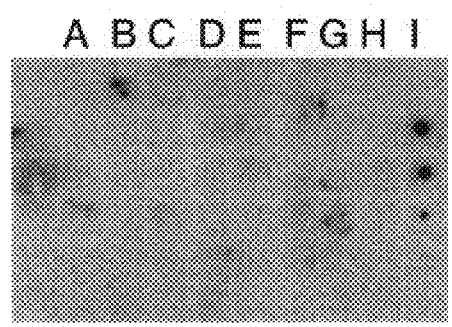
Figure 2:
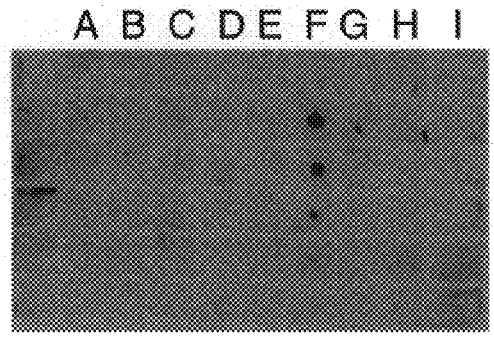

With reference to FIGS. 1, I–V (Species Specific PNA Probes) and FIG. 2, I–V (Genus Specific PNA Probes), total-RNA of each of the following bacteria were spotted on membranes in the columns illustrated: A Pseudomonas fluorescens, B Pseudomonas aeruginosa, C Pseudomonas cepatia, D Pseudomonas putida, E Escherichia coli, F Bacillus subtilis, G Staphylococcus epidermidis, H Staphylococcus aureus, and I Salmonella typhimurium. Individual membranes were placed in plastic bags and pre-wet with RNase free water. The membranes were prehybridized in hybridization buffer (20 mM Tris-HCl, pH 7.5; 50% formamide; 0.1% sodium dodecyl sulfate (SDS); and 100 mM NaCl) for 15 minutes at 50° C.

All probes were diluted in 1:1 DMF/H$_2$O to a concentration of approximately 300 pmole/μL and then diluted to a final concentration of 5 pmol/mL each using Hybridization Buffer. The prehybridization buffer was then removed from the bags and fresh hybridization buffer containing the probe (s) of interest (Flu-1 through Flu-12 as described above), was(were) added to the bags.

The hybridization was performed at 50° C. for 1 hour. The filters were then washed 3 times in TE-7.5 (10 mM Tris-HCl, pH 7.5, 1 mM EDTA) containing 0.2% SDS. The first wash was at room temperature for 5 minutes. The second and third washes were at 65° C. for 10–15 minutes each.

Visualization of the Membrane:
After the washes were completed, the membranes were treated with a blocking solution (50 mM Tris-HCl, pH 9.0; 0.5 M NaCl; and 0.5% casein). The starting temperature of the solution was 65° C., but the solution cooled as the blocking proceeded with shaking at room temperature for 15 minutes. An anti-fluorescein-alkaline phosphatase conjugate (Rabbit (Fab) anti-FITC/AP (DAKO A/S, P/N K0046)) was diluted 1:1000 in blocking solution and the membranes were left shaking in this solution for 30 minutes at room temperature. The membranes were then washed in a washing solution (50 mM Tris-HCl, pH 9.0; 0.5 M NaCl; and 0.5% Tween-20) three times each for 5 minutes. To prepare the membranes for the detection, a final rinse was performed with a rinse solution (10 mM Tris-HCl, pH 9.5; 10 mM NaCl; and 1 mM $MgCl_2$). The chemiluminescent substrate (AMPPD, Tropix Corp., P/N PD025) was diluted 1:100 in an aqueous substrate solution (0.1 M diethanolamine, pH 9.7; and 1 mM $MgCl_2$) and the membranes were immersed without shaking for 4 minutes. The membranes were placed in a plastic bag and excess substrate was squeezed out and the bag sealed. The membranes were exposed to Fuji-RX X-ray film for between 5 and 30 minutes.

With reference to FIGS. 1-I through 1-V, the specificity of the species specific PNA probes was examined. PNA probes Flu-1, Flu-2, Flu-5 and Flu-6 were shown to be specific, within the parameters of the experiment, for the rRNA of the intended target organism (*E. coli, S. aureus, P. cepatia* and *P. fluorescens*, respectively) in the presence of rRNA of the other bacteria spotted on the membrane. The mixture of Flu-3 and Flu-4 was likewise shown to be specific, within the parameters of the experiment, for the rRNA of *Pseudomonas aeruginosa*.

With reference to FIGS. 2-I through 2-IV, the specificity of the genus specific PNA probes was examined. PNA probes, Flu-10, Flu-11 and Flu-12, were shown to be specific, within the parameters of the experiment, for the rRNA of the intended target organism (Salmonella genus and Bacillus genus, respectively) in the presence of rRNA of the other bacteria spotted on the membrane. The mixture of Flu-7, Flu-8 and Flu-9, was likewise shown to be specific, within the parameters of the experiment, for the rRNA of the bacteria of the Pseudomonas genus which were examined.

Example 9

PNA-FISH

Individual 3 mL cultures of bacteria were grown overnight in Tryptic Soy Broth (TSB) at 30° C. The broth was then analyzed for absorbance at 600nm and then diluted into fresh TSB until the absorbance at 600 nm was 0.5 OD/mL. These diluted culture stocks were then allowed to double 3–4 times before harvesting. Cells from a 20 mL culture were pelleted by centrifugation at 8000 rpm for 5 minutes, resuspended in 20 mL PBS, pelleted again and resuspended in Fixation Buffer (3% paraformaldehyde in PBS(7 mM $Na_2HPO_4$; 3 mM $NaH_2PO_4$; 130 mM NaCl)). The bacteria were incubated at room temperature for 30–60 minutes before they were pelleted again (centrifugation at 8000 rpm for 5 minutes). After removal of the fixation solution, the cells were resuspended in 20 mL of 50% aqueous ethanol. The fixed bacteria were then used after 30 minutes of incubation or optionally stored at −20° C. for up to several weeks before being used in an experiment.

For each sample prepared, 100 μl of fixed cells in 50% aqueous ethanol was removed and centrifuged at 8000 R.P.M. for 2 min. The ethanol was then remove from the sample and the pellet was resuspended in 100 μl of sterile PBS and pelleted again by centrifugation at 8000 R.P.M. for 2 min.

The PBS was then removed from the pellet, and the cells were resuspended in 100 μl of hybridization buffer (20 mM Tris-HCl, pH 9.0; 100 mM NaCl; 0.5% SDS) which contained the appropriate probe (e.g. Flu-1 thought Flu-12) at a concentration of 30 pmol/mL. The hybridization was performed at 55° C. for 30 minutes.

The sample was then centrifuged at 8000 R.P.M. for 2 min. The hybridization buffer was removed and the cells resuspended in 500 μl sterile TE-9.0 (10 mM Tris-HCl, pH 9.0; 1 mM EDTA). The solution was allowed to stand at 55° C. for 5 minutes. The sample was then centrifuged at 8000 rpm for 5 minutes. The TE-9.0 was then removed from the pellet. The TE-9.0 wash was then repeated two more times.

After the final wash the cells were resuspended in 100 μl PBS. An aliquot of 2 μl of this suspension of cells was placed on a glass slide, spread and allowed to dry. Next, 1–2 μl of Vectashield (Vector Laboratories, P/N H-1000) was deposited over the dried cells. A coverslip was added to the slide and its position fixed using a couple of drops of nail polish. Each of the nine different bacterial strains, *Pseudomonas fluorescens, Pseudomonas aeruginosa, Pseudomonas cepatia, Pseudomonas putida, Escherichia coli, Bacillus subtilis, Staphylococcus epidermidis, Staphylococcus aureus,* and *Salmonella typhimurium*, were fixed and hybridized with each of probes Flu-1 through Flu-6 following the protocol described above. After hybridization and wash, each strain was spotted and mounted on a microscope slide (see above) and examined using a Nikon fluorescent microscope equipped with a 60× immersion oil objective, a 10× ocular (total enlargement is 600 fold), and an Omega Optical XF22 filter. All probes exhibited an excellent discrimination between the bacteria strain which they were selected to detect, and the other strains tested. Even the detection of Pseudomonas fluorescens using probe Flu-6 showed excellent specificity, despite the low level of cross hybridization observed in the dot blots (see FIG. 1-V). Similarly, hybridization of each of the nine strains with the genus specific probes (#Flu-10 though Flu-12) or probe mnixtures (#Flu-7 through Flu-9) showed excellent specificity for the individual genus tested.

Example 10

Multiplex PNA-FISH

A mixture of the four USP organisms, *E. coli, S. aureus, P. aeruginosa,* and *S. typhimurium*, fixed individually as previously described, was prepared and hybridized with a mixture of four PNA probes comprised of Flu-Rox-1, Rox-2, Flu-4 and Cou-10 (See Table 3). The hybridization protocol was as described in Example 9.

After hybridization and wash, the bacteria were spotted and mounted on a microscope slide (see above) and inspected using a Nikon fluorescent microscope equipped with a 60× immersion oil objective, a 10× ocular (total enlargement is 600 fold) and light filters obtained from Omega Optical (XF22 (green), XF34 (red), and XF05 (blue) filter). Electronic digital images were made of the slide using a SPOT CCD-camera and software obtained from Diagnostic Instruments, Inc., Sterling Heights, Mich. (USA).

The digital images obtained, all covering the same section of the slide, are presented in FIGS. 3-I through 3-IV. In FIG. 3-I (green image), bacteria stained green by the Flu-3 (*P. aeruginosa*) and Flu-Rox-1 (*E. coli*) probes are visible. In FIG. 3-II (red image), bacteria stained red by the Flu-Rox-1

(*E. coli*) and the Rox-2 (*S. aureus*) probes are visible. In FIG. 3-III (blue image), bacteria stained blue by the Cou-10 probe (*S. typhimuritum*) are visible. In FIG. 3-IV, a digital composite of the blue and the red images is presented. This digital composite clearly demonstrates that simultaneous detection of several different bacteria in the same sample (multiplexing) is possible using PNA probes. Though the multiplex analysis described herein is performed manually by visual inspection of the digital images, software is available for performing such a comparison to thereby generate quantitative data for each of the target organisms present in the sample.

EQUIVALENTS

While this invention has been particularly shown and described with references to preferred embodiments thereof, it will be understood by those of ordinary skill in the art that various changes in form and details may be made therein without departing from the spirit and scope of the invention as defined by the appended claims. Those skilled in the art will be able to ascertain, using no more than routine experimentation, many equivalents to the specific embodiments of the invention described herein. Such equivalents are intended to be encompassed in the scope of the claims.

We claim:

1. A PNA probe comprising a probing nucleobase sequence for detecting, identifying or quantitating one or more organisms of interest in a sample wherein the organisms of interest are selected from the group of bacterial species consisting of: Staphylococcus aureus, Pseudomonas aeruginosa, Pseudomonas cepatia, Pseudomonas fluorescens or organisms of a bacterial genus selected from the group consisting of: the Salmonella genus, Bacillus genus or Pseudomonas genus, wherein the probe is labeled with at least two independently detectable moieties.

2. A PNA probe comprising a probing nucleobase sequence for detecting, identifying or quantitating one or more organisms of interest in a sample wherein the organisms of interest are selected from the group of bacterial species consisting of: Staphylococcus aureus, Pseudomonas aeruginosa, Pseudomonas cepatia, Pseudomonas fluorescens or organisms of a bacterial genus selected from the group consisting of: the Salmonella genus, Bacillus genus or Pseudomonas genus, wherein at least a portion of the probing nucleobase sequence is at least ninety percent homologous to the nucleobase sequences selected from the group consisting of:

GCT-TCT-CGT-CCG-TTC (Seq. ID No. 2); CTG-AAT-CCA-GGA-GCA (Seq. ID No. 3); AAC-TTG-CTG-AAC-CAC (Seq. ID No. 4); CCA-TCG-CAT-CTA-ACA (Seq. ID No. 5); TCT-AGT-CAG-TCA-GTT (Seq. ID No. 6); CCG-ACT-TGA-CAG-ACC (Seq. ID No. 10); CCT-GCC-AGT-TTC-GAA (Seq. ID No. 11); CTT-TGT-TCT-GTC-CAT (Seq. ID No. 12); GCT-GGC-CTA-GCC-TTC (Seq. ID No. 7); GTC-CTC-CTT-GCG-GTT (Seq. ID No. 8) and TTC-TCA-TCC-GCT-CGA (Seq. ID No. 9);

and sequences fully complementary and of the same length.

3. The PNA probe of claim 2, wherein the probe is unlabeled.

4. The PNA probe of claim 2, wherein the probe is labeled with at least one detectable moiety.

5. The PNA probe of claim 4, wherein the detectable moiety or moieties are selected from the group consisting of: a dextran conjugate, a branched nucleic acid detection system, a chromophore, a fluorophore, a spin label, a radioisotope, an enzyme, a hapten, an acridinium ester and a chemiluminescent compound.

6. The PNA probe of claim 1, wherein the two or more independently detectable moieties are independently detectable fluorophores.

7. The PNA probe of claim 2, wherein the probe is support bound.

8. A PNA probe set for detecting, identifying or quantitating one or more organisms of interest in a sample wherein the organisms of interest are selected from the group consisting of: E. coli, Staphylococcus aureus, Pseudomonas aeruginosa, Pseudomonas cepatia, Pseudomonas fluorescens and bacteria of the Salmonella genus, Bacillus genus or Pseudomonas genus and wherein at least one PNA probe of the set has a probing nucleobase sequence such that at least a portion is at least ninety percent homologous to the nucleobase sequences selected from the group consisting of:

TCA-ATG-AGC-AAA-GGT (Seq. ID No. 1); GCT-TCT-CGT-CCG-TTC'-(Seq. ID No. 2); CTG-AAT-CCA-GGA-GCA (Seq. ID No. 3); AAC-TTG-CTG-AAC-CAC (Seq. ID No. 4); CCA-TCG-CAT-CTA-ACA (Seq. ID No. 5); TCT-AGT-CAG-TCA-GTT (Seq. ID No. 6); CCG-ACT-TGA-CAG-ACC (Seq. ID No. 10); CCT-GCC-AGT-TTC-GAA (Seq. ID No. 11); CTT-TGT-TCT-GTC-CAT (Seq. ID No. 12); GCT-GGC-CTA-G!CC-TTC (Seq. ID No. 7); GTC-CTC-CTT-GCG-GTT (Seq. ID No. 8) and TTC-TCA-TCC-GCT-CGA (Seq. ID No. 9);

and sequences fully complementary and of the same length.

9. The probe set of claim 8, wherein a PNA probe for E. coli has a probing nucleobase sequence TCA-ATG-AGC-AAA-GGT (Seq. ID No. 1); a PNA probe for Staphylococcus aureus has a probing nucleobase sequence GCT-TCT-CGT-CCG-TTC (Seq. ID No. 2); a PNA probe for Pseudomonas aeruginosa has a probing nucleobase sequence selected from the group consisting of: CTG-AAT-CCA-GGA-GCA (Seq. ID No. 3) and AAC-TTG-CTG-AAC-CAC (Seq. ID No. 4); a PNA probe for Pseudomonas cepatia has a probing nucleobase sequence CCA-TCG-CAT-CTA-ACA (Seq. ID No.5); and a PNA probe for Pseudomonas fluorescens has a probing nucleobase sequence TCT-AGT-CAG-TCA-GTT (Seq. ID No. 6).

10. The probe set of claim 8, wherein a PNA probe for bacteria of the Salmonella genus has a probing nucleobase sequence selected from the group consisting of: CCG-ACT-TGA-CAG-ACC (Seq. ID No. 10) and CCT-GCC-AGT-TTC-GAA (Seq. ID No. 11) a PNA probe for bacteria of the Bacillus genus has a probing nucleobase sequence CTT-TGT-TCT-GTC-CAT (Seq. ID No. 12); and a PNA probe for bacteria of the Pseudomonas genus has a probing nucleobase sequence selected from the group consisting of: GCT-GGC-CTA-GCC-TTC (Seq. ID No. 7), GTC-CTC-CTT-GCG-GTT (Seq. ID No. 8) and TTC-TCA-TCC-GCT-CGA (Seq. ID No. 9).

11. The probe set of claim 10, wherein the probe suitable for detecting bacteria of the Pseudomonas genus will detect Pseudomonas aeruginosa, Pseudomonas cepatia, Pseudomonas fluorescens and Pseudomonas putida.

12. A PNA probe set suitable for detecting, identifying or quantitating one or more USP bacteria in a sample wherein the USP bacteria are selected from the group consisting of: E. coli, the Salmonella genus, Pseudomonas aeruginosa and Staphylococcus aureus and wherein the PNA probes of the set have a probing nucleobase sequence such that at least a portion is at least ninety percent homologous to the nucleobase sequences selected from the group consisting of:

TCA-ATG-AGC-AAA-GGT.(Seq. ID No. 1); CCG-ACT-TGA-CAG-ACC (Seq. ID No. 10); CCT-GCC-AGT-TTC-GAA (Seq. ID No. 11); CTG-AAT-CCA-GGA-GCA (Seq. ID No. 3); AAC-TTG-CTG-AAC-CAC (Seq. ID No. 4) and GCT-TCT-CGT-CCG-TTC (Seq. ID No. 2);

and sequences fully complementary and of the same length.

13. The probe set of claim 12, wherein a PNA probe for E. coli has a probing nucleobase sequence TCA-ATG-AGC-AAA-GGT (Seq. ID No. 1); a PNA probe for Salmonella has a probing nucleobase sequence selected from the group consisting of: CCG-ACT-TGA-CAG-ACC (Seq. ID No. 10) and CCT-GCC-AGT-TTC-GAA (Seq. ID No. 11); a PNA probe for Pseudomonas aeruginosa has a probing nucleobase sequence selected from the group consisting of: CTG-AAT-CCA-GGA-GCA (Seq. ID No. 3) and AAC-TTG-CTG-AAC-CAC (Seq. ID No. 4); and a PNA probe for Staphylococcus aureus has a probing nucleobase sequence GCT-TCT-CGT-CCG-TTC (Seq. ID No. 2).

14. The probe set of claim 12, wherein in situ hybridization is used to detect, identify or quantitate organisms in the sample.

15. The probe set of claim 8, wherein two or more probes of the set are independently detectable.

16. The probe set of claim 8, wherein one or more probes of the set are labeled with two or more independently detectable moieties.

17. The probe set of claim 16, wherein the two or more independently detectable moieties are independently detectable fluorophores.

18. The probe set of claim 11, wherein at least one probe is support bound.

19. A method for detecting, identifying or quantitating one or more organisms of interest in a sample, wherein the organisms of interest are selected from the group consisting of: E. coli, Staphylococcus aureus, Pseudomonas aeruginosa, Pseudomonas cepatia, Pseudomonas fluorescens and bacteria of the Salmonella genus, Bacillus genus or Pseudomonas genus: said method comprising:

a) contacting the sample with one or more PNA probes, wherein the one or more PNA probes have a probing nucleobase sequence such that at least a portion is at least ninety percent homologous to the nucleobase sequences, or their complements, selected from the group consisting of:

TCA-ATG-AGC-AAA-GGT (Seq. ID No. 1); GCT-TCT-CGT-CCG-TTC (Seq. ID No. 2); CTG-AAT-CCA-GGA-GCA (Seq. ID No. 3); AAC-TTG-CTG-AAC-CAC (Seq. ID No. 4); CCA-TCG-CAT-CTA-ACA (Seq. ID No. 5); TCT-AGT-CAG-TCA-GTT (Seq. ID No. 6); CCG-ACT-TGA-CAG-ACC (Seq. ID No. 10); CCT-GCC-AGT-TTC-GAA (Seq. ID No. 11); CTT-TGT-TCT-GTC-CAT (Seq. ID No. 12); GCT-GGC-CTA-GCC-TTC (Seq. ID No. 7); GTC-CTC-CTT-GCG-GTT (Seq. ID No. 8); and TTC-TCA-TCC-GCT-CGA (Seq. ID No. 9);

and sequences fully complementary and of the same length; and b. detecting, identify or quantitating hybridization of the probing nucleobase sequence of the one or more PNA probes to the target sequence of an organism of interest, under suitable hybridization conditions or suitable in-situ hybridization conditions, and correlating the result with the presence, absence or number of the one or more organisms of interest in the sample.

20. The method of claim 19, wherein species of Pseudomonas bacteria including *Pseudomonas aeruginosa, Pseudomonas cepatia* and *Pseudomonas fluorescens* are detected, identified or quantitated by:
 a) contacting the sample with one or more PNA probes, wherein at least one probe of the set has a probing nucleobase sequence such that at least a portion is at least ninety percent homologous to the nucleobase sequences selected from the group consisting of:
  CTG-AAT-CCA-GGA-GCA (Seq. ID No. 3); AAC-TTG-CTG-AAC-CAC (Seq. ID No. 4); CCA-TCG-CAT-CTA-ACA (Seq. ID No. 5; and TCT-AGT-CAG-TCA-GTT (Seq. ID No. 6) and sequences fully complementary and of the same length; and
 b) detecting, identify or quantitating hybridization of the probing nucleobase sequence of the one or more PNA probes to the target sequence of an organism of interest, under suitable hybridization conditions or suitable in-situ hybridization conditions, and correlating the result with the presence, absence or number of one or more species of Pseudomonas in the sample.

21. The method of claim 19, wherein bacteria of the Pseudomonas genus are detected, identified or quantitated by:
 a) contacting the sample with one or more PNA probes, wherein at least one probe of the set has a probing nucleobase sequence such that at least a portion is at least ninety percent homologous to the nucleobase sequences selected from the group consisting of:
  GCT-GGC-CTA-GCC-TTC (Seq. ID No. 7); GTC-CTC-CTT-GCG-GTT (Seq. ID No. 8); and TTC-TCA-TCC-GCT-CGA (Seq. ID No. 9); and sequences fully complementary and of the same length; and
 b) detecting, identify or quantitating hybridization of the probing nucleobase sequence of the one or more PNA probes to the target sequence of an organism of interest, under suitable hybridization conditions or suitable in-situ hybridization conditions, and correlating the result with the presence, absence or number of Pseudomonas bacteria in the sample.

22. The method of claim 19, wherein one or more USP bacteria in the sample are detected, identified or quantitated by:
 a) contacting the sample with one or more PNA probes, wherein at least one probe of the set has a probing nucleobase sequence such that at least a portion is at least ninety percent homologous to the nucleobase sequences selected from the group consisting of:
  TCA-ATG-AGC-AAA-GGT (Seq. ID No. 1); CCG-ACT-TGA-CAG-ACC (Seq. ID No. 10); CCT-GCC-AGT-TTC-GAA (Seq. ID No. 11); CTG-AAT-CCA-GGA-GCA (Seq. ID No. 3); AAC-TTG-CTG-AAC-CAC (Seq. ID No. 4); and GCT-TCT-CGT-CCG-TTC (Seq. ID No. 2); and sequences fully complementary and of the same length; and
 a) detecting, identify or quantitating hybridization of the probing nucleobase sequence of the one or more PNA probes to the target sequence of an organism of interest, under suitable hybridization conditions or suitable in-situ hybridization conditions, and correlating the result with the presence, absence or number of the one or more USP organisms of interest in the sample.

23. The method of claim 19, wherein in situ hybridization using a fluorophore or enzyme-linked probe is used to detect or identify the presence, absence or number of organisms in the sample.

24. The method of claim 19, wherein two or more PNA probes are independently detectable.

25. The method of claim 19, wherein one or more probes of the set are labeled with two or more independently detectable moieties.

26. The method of claim 25, wherein the two or more independently detectable moieties are independently detectable fluorophores.

27. The method of claim 25, wherein at least one PNA probe is support bound.

28. A kit suitable for performing an assay which detects the presence, absence or number of one or more organisms of interest in a sample, wherein said kit comprises:
 a) one or more PNA probes, wherein the PNA probes have a probing nucleobase sequence such that at least a portion is at least ninety percent homologous to the nucleobase sequences selected from the group consisting of:
  TCA-ATG-AGC-AAA-GGT (Seq. ID No. 1); GCT-TCT-CGT-CCG-TTC (Seq. ID No. 2); CTG-AAT-CCA-GGA-GCA (Seq. ID No. 3); AAC-TTG-CTG-AAC-CAC (Seq. ID No. 4); CCA-TCG-CAT-CTA-ACA (Seq. ID No. 5); TCT-AGT-CAG-TCA-GTT (Seq. ID No. 6); CCG-ACT-TGA-CAG-ACC (Seq. ID No. 10); CCT-GCC-AGT-TTC-GAA (Seq. ID No. 11); CTT-TGT-TCT-GTC-CAT (Seq. ID No. 12); GCT-GGC-CTA-GCC-TTC (Seq. ID No. 3; GTC-CTC-CTT-GCG-GTT (Seq. ID No. 8) and TTC-TCA-TCC-GCT-CGA (Seq. ID No. 9) and sequences fully complementary and of the same length; and
 b) other reagents or compositions necessary to perform the assay.

29. The kit of claim 28, wherein the kit is used for the detection, identification or quantitation of one or more organisms selected from the group consisting of: *E. coli, Staphylococcus aureus, Pseudomonas aeruginosa, Pseudomonas cepatia, Pseudomonas fluorescens* and bacteria of the Salmonella genus, Bacillus genus or Pseudomonas genus.

30. The kit of claim 28, wherein the kit is used for the species specific or general detection or quantitation of bacteria of the Pseudomonas genus.

31. The kit of claim 28, wherein the probes of the kit are unlabeled.

32. The kit of claim 28, wherein at least one probe is labeled with a detectable moiety.

33. The kit of claim 28, wherein two or more probes are labeled with independently detectable moieties.

34. The kit of claim 28, wherein at least one probe is labeled with at least two independently detectable moieties.

35. The kit of claim 34, wherein the two or more independently detectable moieties are independently detectable fluorophores.

36. The kit of claim 31, wherein hybridization of the probing nucleobase sequence of the probe to the nucleic acid of the organism of interest is detected using an antibody or antibody fragment, wherein the antibody or antibody fragment specifically binds to the PNA/nucleic acid complex.

37. The kit of claim 36, comprising an antibody labeled with a detectable moiety.

38. The kit of claim 37, wherein the detectable moiety is selected from the group consisting of a dextran conjugate, a branched nucleic acid detection system, a chromophore, a fluorophore, a spin label, a radioisotope, an enzyme, a hapten, an acridinium ester and a chemiluminescent compound.

39. The kit of claim 28, wherein the kit is designed to perform an in-situ hybridization assay.

40. The kit of claim 28, wherein the kit is used to detect organisms in food, beverages, water, pharmaceutical products, personal care products, dairy products, environmental samples or clinical samples.

41. The kit of claim 40, wherein the beverages include soda, bottled water, fruit juice, beer, wine or liquor products.

42. The kit of claim 28, wherein the kit is used to test raw materials, products or processes.

43. A PNA probe having a probing nucleobase sequence that is at least ninety percent homologous to the nucleobase sequence: TCA-ATG-AGC-AAA-GGT (Seq. ID No. 1); and the sequence fully complementary thereto and of the same length.

44. The probe set of claim 12, wherein two or more probes of the set are independently detectable.

45. The probe set of claim 12, wherein one or more probes of the set are labeled with two or more independently detectable moieties.

46. The probe set of claim 45, wherein the two or more independently detectable moieties are independently detectable fluorophores.

47. The probe set of claim 14, wherein at least one probe is support bound.

* * * * *